(12) United States Patent
Chaves et al.

(10) Patent No.: US 8,158,812 B2
(45) Date of Patent: Apr. 17, 2012

(54) DIOL-DERIVED ORGANOFUNCTIONAL SILANE AND COMPOSITIONS CONTAINING SAME

(75) Inventors: Antonio Chaves, Chappaqua, NY (US); Richard W. Cruse, Yorktown Heights, NY (US); Eric Raymond Pohl, Mount Kisco, NY (US)

(73) Assignee: Momentive Performance Marerials Inc., Albany, NY (US)

( * ) Notice: Subject to any disclaimer, the term of this patent is extended or adjusted under 35 U.S.C. 154(b) by 0 days.

(21) Appl. No.: 13/105,297

(22) Filed: May 11, 2011

(65) Prior Publication Data

US 2011/0213074 A1   Sep. 1, 2011

Related U.S. Application Data

(63) Continuation of application No. 11/104,103, filed on Apr. 12, 2005, now Pat. No. 7,960,576.

(51) Int. Cl.
*C07F 7/08*   (2006.01)
(52) U.S. Cl. ............. 556/406; 556/9; 556/12; 556/400; 525/100; 528/20
(58) Field of Classification Search .................. None
See application file for complete search history.

(56) References Cited

U.S. PATENT DOCUMENTS

| | | | |
|---|---|---|---|
| 3,856,756 A | 12/1974 | Wagner et al. ............. 528/49 |
| 3,946,059 A * | 3/1976 | Janssen et al. ............. 556/428 |
| 4,044,037 A | 8/1977 | Mui et al. | |
| 4,045,459 A * | 8/1977 | Foery et al. ............. 556/446 |
| 4,290,869 A * | 9/1981 | Pigeon ............. 428/438 |
| 4,595,740 A | 6/1986 | Panster | |
| 5,674,932 A | 10/1997 | Agostini et al. | |
| 5,981,674 A | 11/1999 | Schombourg et al. | |
| 6,172,251 B1 | 1/2001 | Parker | |
| 6,331,605 B1 | 12/2001 | Lunginsland et al. | |
| 7,326,753 B2 | 2/2008 | Weller | |
| 2006/0178487 A1 | 8/2006 | Weller | |

FOREIGN PATENT DOCUMENTS

| | | |
|---|---|---|
| DE | 19957325 | 5/2001 |
| EP | 0 068 813 | 1/1983 |
| EP | 0211154 | 2/1987 |
| EP | 0784072 A | 7/1997 |
| EP | 1002835 A | 5/2000 |
| FR | 2 382 456 | 9/1978 |
| FR | 2382456 | 9/1978 |
| GB | 1 371 804 | 10/1974 |
| GB | 2 315 688 | 2/1998 |
| RU | 2123016 | 12/1998 |
| WO | WO 99/09036 | 2/1999 |
| WO | WO 2004/045552 | 6/2004 |

OTHER PUBLICATIONS

Marsden J G, "Organofunctional Silane Coupling Agents", *Handbook of Adhesives*, pp. 536-555 (1990).
Notification of Transmittal of International Search Report, PCT/US2005/025068, dated Dec. 23, 2005.
Chemical Abstract, vol. 133, No. 164751, Sep. 1, 2000, Columbus, Ohio. U.S. Abstract No. :2000:607472. Katova, SA; OSIPCHIK, V.S., Lebedeva, ED., Vasilets, L.G. "Crosslinking composition based on high density polyethylene and vinyltris(beta-ethoxyethoxy)silane" XP002387517 Abstract.

* cited by examiner

*Primary Examiner* — Sudhakar Katakam
(74) *Attorney, Agent, or Firm* — Dominick G. Vicari; Joseph S. Ostroff

(57) ABSTRACT

Described are diol-derived organofunctional silanes in which the silanes contain cyclic and bridged alkoxy groups derived from hydrocarbon-based diols and methods for the preparation of the silanes. Also described are rubber compositions containing the diol-derived organofunctional silanes, methods for the preparation of the rubber compositions and articles of manufacture containing the rubber compositions, in particular, automotive tires and components thereof.

30 Claims, No Drawings

DIOL-DERIVED ORGANOFUNCTIONAL SILANE AND COMPOSITIONS CONTAINING SAME

CROSS-REFERENCE TO RELATED APPLICATION

This is a continuation of U.S. patent application Ser. No. 11/104,103 filed Apr. 12, 2005, now allowed, to which priority is claimed and which is herein incorporated by reference.

BACKGROUND OF THE INVENTION

A large body of prior art exists in conjunction with the composition of matter, preparation and uses of silane compounds and to a lesser extent, organofunctional silanes, in rubber and other applications. For instance, the prior art describes reactions of difunctional and trifunctional methylsilanes with diols and triols. It is also known in the art that when difunctional silanes are reacted with ethylene glycol, cyclic dimers are obtained although no cyclic monomers are reported. In addition, when other glycols are reacted with difunctional silanes polymers are obtained.

Also known in the art are bicyclic compounds prepared from tetrafunctional silanes and glycols, as well as bicyclic compounds prepared from dimethyldialkoxysilanes and pentaerythritol. However, these compounds do not have organofunctional groups on the silane and are not useful as coupling agents, crosslinkers or adhesion promoters.

The prior art describes cyclic compounds with dimethyldialkoxysilanes and dimethyl- and methylvinylalkoxysilanes with 2-butene-1,4-diol that form a cyclic compound, which are used as parasiticides.

Furthermore, the transesterification of alkoxysilanes with ethylene glycol to give non-cyclic silane compounds, which are soluble in water and insoluble in benzene, is known in the art. These non-cyclic silane compounds are used as masonry water repellents.

Also described in the prior art is the preparation of cyclic silanes from the reaction of dimethyldialkoxysilanes with glycerin. These materials polymerize spontaneously at room temperature to give polymeric materials with high viscosity.

Cyclic glycol esters of difunctional alkenyl silanes that are useful additives in the production of organopolysiloxane adhesive compositions have also been described in the art.

The above-mentioned prior art does not address the use of silane containing organofunctional groups with reduced volatile organic compound, referred herein as VOC, or no VOC by the use of heterocyclic silicon groups. Accordingly, there exists a need for improved silanes.

SUMMARY OF THE INVENTION

In accordance with one embodiment of the present invention, a silane composition is provided comprising:

 (Formula 1)

wherein each occurrence of G is independently chosen from a set of groups comprising a polyvalent group derived by substitution of one or more hydrogen atoms of an alkyl, alkenyl, aryl or aralkyl group, or a molecular component which can be obtained by removal of one or more hydrogen atoms of a heterocarbon, with G containing from about 1 to about 30 carbon atoms; each occurrence of X is independently selected from the group consisting of —Cl, —Br, $R^1O$—, $R^1C(=O)O$—, $R^1R^2C=NO$—, $R^1R^2NO$— or $R^1R^2N$—, —$R^1$, —$(OSiR^1R^2)_t(OSiR^1R^2R^3)$, and —$O(R^{10}CR^{11})_fOH$, wherein each occurrence of $R^1$, $R^2$, $R^3$, $R^{10}$, and $R^{11}$ is independently R; each occurrence of $Z^b$ is independently (—O—)$_{0.5}$, and [—O($R^{10}CR^{11}$)$_f$O—]$_{0.5}$, wherein each occurrence of $R^{10}$ and $R^{11}$ is independently R; each occurrence of $Z^c$ is independently given by —O($R^{10}CR^{11}$)$_f$O— wherein each occurrence of $R^0$ and $R^{00}$ is independently R; each occurrence of R is chosen independently from the set of groups comprising hydrogen; straight, cyclic or branched alkyl groups and may contain unsaturated, alkenyl groups, aryl groups, and aralkyl groups; or molecular components obtained by removal of one or more hydrogen atoms of a heterocarbon; each occurrence of R containing 1 to about 20 carbon atoms; each occurrence of the subscript f is an integer from 1 to about 15, each occurrence of n is an integer from 1 to about 100, with the proviso that when n is greater than 1, v is a greater than 0 and all the valences for $Z^b$ have a silicon atom bonded to them, each occurrence of the subscript u is an integer from 0 to about 3, each occurrence of the subscript v is an integer from 0 to about 3, each occurrence of the subscript w is an integer from 0 to about 1, with the proviso that u+v+2w=3, each occurrence of the subscript r is an integer from 1 to about 6, each occurrence of the subscript t is an integer from 0 to about 50, and each occurrence of the subscript s is an integer from 1 to about 6; and each occurrence of Y is an organofunctional group of valence r; and at least one cyclic and bridging dialkoxy organofunctional silane comprising the cyclic and bridging dialkoxy organofunctional silane composition containing at least one occurrence of $Z^b$ or $Z^c$.

In accordance with a second embodiment of the present invention, a process for the preparation of a silane composition is provided comprising reacting at least one organofunctional silane with a diol in the presence or absence of catalyst to provide a diol-derived organofunctional silane.

In accordance with a third embodiment of the present invention, a rubber composition is provided comprising (a) a rubber component; (b) a filler; and (c) at least one silane composition of the general formula

 (Formula 1)

wherein Y, G, X, u, $Z^b$, v, $Z^c$, w, s, n and r have the aforestated meanings.

In accordance with a fourth embodiment of the present invention, a process for preparing a rubber composition is provided comprising adding to a rubber composition reaction-forming mixture an effective amount of at least one silane composition of the general formula

 (Formula 1)

wherein Y, G, X, u, $Z^b$, v, $Z^c$, w, s, n and r have the aforestated meanings.

In accordance with a fifth embodiment of the present invention, articles of manufacture, in particular automotive tires and tire treads, are described as manufactured with a rubber composition herein.

In accordance with a sixth embodiment of the present invention, the silane compounds of the general formula

 (Formula 1)

wherein Y, G, X, u, $Z^b$, v, $Z^c$, w, s, n and r have the aforestated meanings are useful as crosslinkers, coupling agents, adhesion promoters and as filler treating agents. Illustrative compositions into which the silane compounds may be incorporated include rubber, industrial and architectural coatings, wood coatings, hard coats, adhesion promoting primers for paints or adhesives, UV or EB cured acrylic coatings, adhesives and sealants, polyester resin systems used to form reinforced composites with fiberglass, carbon or polyphenylene terephalamide (Kevlar™, E.I. DuPont, Wilm., Del.) reinforcements, room temperature vulcanizable (RTV) silicones, and generally in any application where an organofunctional silane would be used. As is clear to one of ordinary skill in the art, there is a vast array of applications of the present invention in rubber, coating, sealant, adhesives, masonry sealers, fiberglass binders and sizes, inks and other systems that typically use organofunctional silanes.

DETAILED DESCRIPTION OF THE INVENTION

Group Y herein includes univalent organofunctional groups (r=1), divalent organofunctional groups (r=2), trivalent organofunctional groups (r=3), tetravalent organofunctional groups (r=4), as well as organofunctional groups of higher valency, herein referred to as polyvalent organofunctional groups. The term polyvalent organofunctional group herein shall be understood to include univalent, divalent, trivalent, and tetravalent organofunctional groups.

Another embodiment of the present invention herein includes univalent organofunctional groups such as mercapto and acyloxy groups such as acryloxy, methacryloxy and acetoxy. Another embodiment of the present invention herein includes univalent epoxys such as glycidoxy, —O—$CH_2$—$C_2H_3O$; epoxycyclohexylethyl, —$CH_2$—$CH_2$—$C_6H_9O$; epoxycyclohexyl, —$C_6H_9O$; epoxy, —$CR^6$(—O—)$CR^4R^5$. Another embodiment of the present invention herein includes univalent organofunctional groups such as hydroxy, carbamate, —$NR^4C$(=O)$OR^5$; urethane, —OC(=O)$NR^4R^5$; thiocarbamate, —$NR^4C$(=O)$SR^5$; thiourethane, —SC(=O)$NR^4R^5$; thionocarbamate, —$NR^4C$(=S)$OR^5$; thionourethane, —OC(=S)$NR^4R^5$; dithiocarbamate, —$NR^4C$(=S)$SR^5$; and dithiourethane, —SC(=S)$NR^4R^5$. Another embodiment of the present invention herein includes univalent organofunctional groups such as maleimide; maleate and substituted maleate; fumurate and substituted fumurate; nitrile, CN; citraconimide. Another embodiment of the present invention herein includes univalent organofunctional groups such as cyanate, —OCN; isocyanate, —N=C=O; thiocyanate, —SCN; isothiocyanate, —N=C=S; and ether, —$OR^4$. Another embodiment of the present invention herein includes univalent organofunctional groups such as fluoro, —F; chloro, —Cl; bromo, —Br; iodo, —I; and thioether, —$SR^4$. Another embodiment of the present invention herein includes univalent organofunctional groups such as disulfide, —S—$SR^4$; trisulfide, —S—S—$SR^4$; tetrasulfide, —S—S—S—$SR^4$; pentasulfide, —S—S—S—S—$SR^4$; hexasulfide, —S—S—S—S—S—$SR^4$; and polysulfide, —$S_xR^4$. Another embodiment of the present invention herein includes univalent organofunctional groups such as xanthate, —SC(=S)$OR^4$; trithiocarbonate, —SC(=S)$SR^4$; dithiocarbonate, —SC(=O)$SR^4$; ureido, —$NR^4C$(=O)$NR^5R^6$; thionoureido (also better known as thioureido), —$NR^4C$(=S)$NR^5R^6$; amide, $R^4C$(=O)$NR^5$— and —C(=O)$NR^4R^5$—; thionoamide (also better known as thioamide), $R^4C$(=S)$NR^4$—; univalent melamino; and, univalent cyanurato. Another embodiment of the present invention herein includes univalent organofunctional groups such as primary amino, —$NH_2$; secondary amino, —$NHR^4$; and tertiary amino, —$NR^4R^5$. univalent diamino, —$NR^4$-$L^1$-$NR^5R^6$; univalent triamino, —$NR^4$-$L^1$-(—$NR^5R^6$)$_2$ and —$NR^4$-$L^1$-$NR^5$-$L^2$-$NR^6R^7$; and univalent tetraamino, —$NR^4$-$L^1$-(—$NR^5R^6$)$_3$, —$NR^{4-L1}$-$NR^5$-$L^2$-$NR^6$-$L^3$-$NR^7R^8$, and —$NR^4$-$L^1$-N(-$L^2NR^5R^6$)$_2$; wherein each occurrence of $L^1$, $L^2$, and $L^3$ is selected independently from the set of structures given above for G; each occurrence of $R^4$, $R^5$, $R^6$, $R^7$ and $R^8$ is independently given by one of the structures listed above for R; and each occurrence of the subscript, x, is independently given by x is 1 to 10.

Another embodiment of the present invention herein includes divalent organofunctional groups such as epoxy, -(-)C(—O—)$CR^4R^5$ and —$CR^5$(—O—)$CR^4$—. Another embodiment of the present invention herein includes divalent organofunctional groups such as carbamate, -(-)NC(=O)$OR^5$; urethane, —OC(=O)$NR^4$—; thiocarbamate, -(-) NC(=O)$SR^5$; thiourethane, —SC(=O)$NR^4$—; thionocarbamate, -(-)NC(=S)$OR^5$; thionourethane, —OC(=S)$NR^4$—; dithiocarbamate, -(-) NC(=S)$SR^5$; dithiourethane, —SC(=S)$NR^4$—; and ether, —O—. Another embodiment of the present invention herein includes divalent organofunctional groups such as maleate and substituted maleate; fumurate and substituted fumurate. Another embodiment of the present invention herein includes thioether, —S—; disulfide, —S—S—; trisulfide, —S—S—S—; tetrasulfide, —S—S—S—S—; pentasulfide, —S—S—S—S—S—; hexasulfide, —S—S—S—S—S—S—; and polysulfide, —$S_x$—. Another embodiment of the present invention herein includes divalent organofunctional groups such as xanthate, —SC(=S)O—; trithiocarbonate, —SC(=S)S—; dithiocarbonate, —SC(=O)S—; ureido, -(-)NC(=O)$NR^4R^5$ and —$NR^4C$(=O)$NR^5$—; thionoureido, also better known as thioureido, -(-) NC(=S)$NR^4R^5$ and —$NR^4C$(=S)$NR^5$—; amide, $R^4C$(=O)N(-)- and —C(=O)$NR^4$—; thionoamide, also better known as thioamide, $R^4C$(=S)N(-)-; divalent melamino; divalent cyanurato. Another embodiment of the present invention herein includes divalent organofunctional groups such as secondary amino, —NH—; tertiary amino, —$NR^4$—; divalent diamino, -(-)N-$L^1$-$NR^4R^5$ and —$NR^4$-$L^1$-$NR^5$—; divalent triamino, (-) $NR^4$)$_2$-$L^1$-$NR^5R^6$, -(-)N-$L^1$-$NR^5$-$L^2$-$NR^6R^7$, —$NR^4$-$L^1$-N(-)-$L^2$-$NR^5R^6$, and —$NR^4$-$L^1$-$NR^5$-$L^2$-$NR^6$—; and divalent tetraamino, -(-)N-$L^1$-($NR^5R^6$)$_3$, (—$NR^4$)$_2$-$L^1$-($NR^5R^6$)$_2$, -(-)N-$L^1$-$NR^4$-$L^2$-$NR^5$-$L^3$-$NR^6R^7$, —$NR^4$-$L^1$-N(-)-$L^2$-$NR^5$-$L^3$-$NR^6R^7$, —$NR^4$-$L^1$-$NR^5$-$L^2$-N(-)-$L^3$-$NR^6R^7$, —$NR^4$-$L^1$-$NR^5$-$L^2$-$NR^6$-$L^3$-$NR^7$—, -(-)N-$L^1$-N(-$L^2NR^5R^6$)$_2$, and (—$NR^4$-$L^1$-)$_2$N-$L^2NR^5R^6$; wherein each occurrence of $L^1$, $L^2$, and $L^3$ is selected independently from the set of structures given above for G; each occurrence of $R^4$, $R^5$, $R^6$, and $R^7$ is independently given by one of the structures listed above for R; and each occurrence of the subscript, x, is independently given by x is 1 to 10.

Another embodiment of the present invention herein includes trivalent organofunctional groups such as epoxy, -(-)C(—O—)$CR^4$—. Another embodiment of the present invention herein includes trivalent organofunctional groups such as hereincarbamate, -(-) NC(=O)O—; thiocarbamate, -(-) NC(=O)S—; thionocarbamate, -(-)NC(=S)O—; and dithiocarbamate, -(-)NC(=S)S—. ureido, -(-) NC(=O)$NR^4$—; thionoureido, also better known as thioureido, -(-)NC(=S)$NR^4$—; amide, —C(=O)N (-)-; thionoamide, also better known as thioamide, —C(=S)N(-)-; trivalent melamino; and trivalent cyanurato. Another embodiment of the present invention herein includes trivalent organofunctional groups such as tertiary amino, —N(-)-; trivalent diamino, -(-)N-$L^1$-$NR^4$—; trivalent triamino, (—$NR^4$)$_3$-$L^1$, (—$NR^4$)$_2$-$L^1$-$NR^5$—, -(-)N-$L^1$-N(-)-$L^2$-$NR^3R^4$, —$NR^4$-$L^1$-N(-)-$L^2$-$NR^5$—, and -(-)N-$L^1$-$NR^4$-$L^2$-$NR^5$—; and trivalent tetraamino, -(-)N-$L^1$-N(-)-$L^2$-$NR^5$-$L^3$-$NR^3R^4$, —$NR^4$-$L^1$-N(-)-$L^2$-N(-)-$L^3$-$NR^3R^4$, -(-)N-$L^1$-$NR^5$-$L^2$-N(-)-$L^3$-$NR^3R^4$, —$NR^4$-$L^1$-N(-)-$L^2$-$NR^3$-$L^3$-$NR^4$—, -(-)N-$L^1$-N(-$L^2NR^3R^4$)(-$L^2NR^5$—), and (—$NR^4L^1$-)$_3$N; wherein each occurrence of $L^1$, $L^2$, and $L^3$ is selected independently from the set of structures given above for G; and each occurrence of $R^4$, $R^5$, and $R^6$ is independently given by one of the structures listed above for R.

Another embodiment of the present invention herein includes tetravalent organofunctional group such as epoxy, -(-)C(—O—)C(-)-; Another embodiment of the present invention herein includes tetravalent organofunctional groups such as ureido, -(-)NC(=O)N(-)-; thionoureido (also better known as thioureido), -(-)NC(=S)N(-)-; and tetravalent melamino. Another embodiment of the present invention herein includes tetravalent organofunctional groups tetravalent diamino, -(-)N-$L^1$-N(-)-; tetravalent triamino, (—$NR^4$)$_4$-$L^1$, (—$NR^4$)$_2$-$L^1$-N(-)-, -(-)N-$L^1$-N(-)-$L^2$-$NR^3$—, and -(-)N-$L^1$-$NR^4$-$L^2$(-)-; and tetravalent tetraamino, -(-)N-$L^1$-N(-)-$L^2$-N(-)-$L^3$-$NR^4R^3$, —$NR^4$-$L^1$-N(-)-$L^2$-N(-)-$L^3$-$NR^3$—, -(-)N-$L^1$-$NR^4$-$L^2$-$NR^3$-$L^3$-N(-)-, and -(-)N-$L^1$-N(-$L^2NR^3$—)$_2$; wherein each occurrence of $L^1$, $L^2$, and $L^3$ is selected independently from the set of structures given above for G; and each occurrence of $R^4$ and $R^5$ is independently given by one of the structures listed above for R.

Another embodiment of the present invention herein includes polyvalent organofunctional groups such as, but is not limited to, polyvalent hydrocarbon groups; pentavalent melamino, (—$NR^3$)(—N—)$_2C_3N_3$; hexavalent melamino, (—N—)$_3C_3N_3$; pentavalent triamino, -(-)N-$L^1$-N(-)-$L^2$-N(-)-; pentavalent tetraamino, -(-)N-$L^1$-N(-)-$L^2$-N(-)-$L^3$-$NR^3$—, -(-)N-$L^1$-$NR^3$-$L^2$-N(-)-$L^3$-N(-)-, and [-(-)N-$L^1$-]$_2$N-$L^2NR^3$—; and hexavalent tetraamino, -(-)N-$L^1$-N(-)-$L^2$-N(-)-$L^3$-N(-)- and [-(-)N-$L^1$-]$_3$N; wherein each occurrence of $L^1$, $L^2$, and $L^3$ is selected independently from the set of structures given above for G; and each occurrence of $R^4$ is independently given by one of the structures listed above for R.

As used herein, diol, hydrocarbon diol, and difunctional alcohol refer to any structure given by Formula 2:

$$HO(R^{10}CR^{11})_fOH \qquad \text{(Formula 2)}$$

wherein f, $R^{10}$, and $R^{11}$ are as defined above. These structures represent hydrocarbons or heterocarbons in which two hydrogen atoms are replaced with OH in accordance with the structures drawn in Formula 2. As used herein, dialkoxy and difunctional alkoxy refer to any hydrocarbon diol, as defined herein, in which the hydrogen atoms of the two OH groups have been removed to a give divalent radical, and whose structure is given by Formula 3:

$$—O(R^{10}CR^{11})_fO— \qquad \text{(Formula 3)}$$

wherein f, $R^{10}$, and $R^{11}$ are as defined above. As used herein, cyclic dialkoxy refers to a silane or group in which cyclization is about silicon, by two oxygen atoms each attached to a common divalent hydrocarbon or heterocarbon group, such as is commonly found in diols. Cyclic dialkoxy groups herein are represented by $Z^c$. As used herein, bridging dialkoxy refers to a silane or group in which two different silicon atoms are each bound to one oxygen atom, which is in turn bound to a common divalent hydrocarbon or heterocarbon group as defined herein, such as is commonly found in diols. Bridging dialkoxy groups herein are represented by $Z^b$. As used herein, cyclic and bridging refers to a silane or group encompassing cyclic only, without bridging; bridging only, without cyclic; and any combination of both cyclic and bridging. Thus, a cyclic and bridging silane could mean, for example, a silane with a silicon atom bound to a cyclic dialkoxy group, a silane with a silicon atom not bound to a cyclic dialkoxy group and bound to bridging dialkoxy group(s) only, a silane with silicon bound to both one end of a bridging dialkoxy group and both ends of a cyclic dialkoxy group, a silane with a silicon atom not bound at all to a dialkoxy group (as long as at least one other silicon atom in the same molecule is bound to at least one cyclic or bridging dialkoxy group), etc. As used herein, hydrocarbon based diols refer to diols, which contain two OH groups on a hydrocarbon or heterocarbon structure. The term, "hydrocarbon based diol", refers to the fact that the backbone between the two oxygen atoms consists entirely of carbon atoms, carbon-carbon bonds between the carbon atoms, and two carbon-oxygen bonds encompassing the alkoxy ends. The heterocarbons in the structure occur pendent to the carbon backbone.

The structures given by Formula 2 will herein be referred to as the appropriate diol, in a few specific cases, glycol is the more commonly used term, prefixed by the particular hydrocarbon or heterocarbon group associated with the two OH groups. Examples include neopentylglycol, 1,3-butanediol, and 2-methyl-2,4-pentanediol. The groups whose structures are given by Formula 3 will herein be referred to as the appropriate dialkoxy, prefixed by the particular hydrocarbon or heterocarbon group associated with the two OH groups. Thus, for example, the diols, neopentylglycol, 1,3-butanediol, and 2-methyl-2,4-pentanediol correspond herein to the dialkoxy groups, neopentylglycoxy, 1,3-butanedialkoxy, and 2-methyl-2,4-pentanedialkoxy, respectively.

The cyclic and bridging dialkoxy organofunctional silanes used herein, in which the silane is derived from a diol, commonly referred to as a glycol, are correspondingly glycoxysilane. Also, the cyclic and bridging organofunctional dialkoxy silanes used herein, in which the silane is derived from a diol, commonly referred to as a diol, are correspondingly named dialkoxysilane.

As used herein, the notations, (—O—)$_{0.5}$ and [—O($R^{10}CR^{11}$)$_f$O—]$_{0.5}$, refer to one half of a siloxane group, Si—O—Si, and one half of a bridging dialkoxy group, respectively. These notations are used in conjunction with a silicon atom and they are taken herein to mean one half of an oxygen atom, namely, the half bound to the particular silicon atom, or to one half of a dialkoxy group, namely, the half bound to the particular silicon atom, respectively. It is understood that the other half of the oxygen atom or dialkoxy group and its bond to silicon occurs somewhere else in the overall molecular structure being described. Thus, the (—O—)$_{0.5}$ siloxane groups and the [—O($R^{10}CR^{11}$)$_f$O—]$_{0.5}$ dialkoxy groups mediate the chemical bonds that hold two separate silicon atoms together, whether these two silicon atoms occur intermolecularly or intramolecularly. In the case of [—O($R^{10}CR^{11}$)$_f$O—]$_{0.5}$, if the hydrocarbon group, ($R^{10}CR^{11}$)$_f$, is unsymmetrical, either end of [—O($R^{10}CR^{11}$)$_f$O—]$_{0.5}$ may be bound to either of the two silicon atoms required to complete the structures given in Formula 1.

As used herein, alkyl includes straight, branched and cyclic alkyl groups; alkenyl includes any straight, branched, or cyclic alkenyl group containing one or more carbon-carbon double bonds, where the point of substitution can be either at a carbon-carbon double bond or elsewhere in the group. Also, alkynyl includes any straight, branched, or cyclic alkynyl group containing one or more carbon-carbon triple bonds and optionally also one or more carbon-carbon double bonds as well, where the point of substitution can be either at a carbon-carbon triple bond, a carbon-carbon double bond, or elsewhere in the group. Specific examples of alkyls include methyl, ethyl, propyl, isobutyl. Specific examples of alkenyls include vinyl, propenyl, allyl, methallyl, ethylidenyl norbornane, ethylidene norbornyl, ethylidenyl norbornene and ethylidene norbornenyl. Specific examples of alkynyls include acetylenyl, propargyl and methylacetylenyl.

As used herein, aryl includes any aromatic hydrocarbon from which one hydrogen atom has been removed; aralkyl includes any of the aforementioned alkyl groups in which one or more hydrogen atoms have been substituted by the same number of like and/or different aryl (as defined herein) substituents; and arenyl includes any of the aforementioned aryl groups in which one or more hydrogen atoms have been substituted by the same number of like and/or different alkyl (as defined herein) substituents. Specific examples of aryls include phenyl and naphthalenyl. Specific examples of aralkyls include benzyl and phenethyl. Specific examples of arenyls include tolyl and xylyl.

As used herein, cyclic alkyl, cyclic alkenyl and cyclic alkynyl also include bicyclic, tricyclic, and higher cyclic structures, as well as the aforementioned cyclic structures further substituted with alkyl, alkenyl and/or alkynyl groups. Representative examples include norbornyl, norbornenyl, ethylnorbornyl, ethylnorbornenyl, ethylcyclohexyl, ethylcyclohexenyl, cyclohexylcyclohexyl, and cyclododecatrienyl.

As used herein, the term, heterocarbon, refers to any hydrocarbon structure in which the carbon-carbon bonding backbone is interrupted by bonding to atoms of nitrogen and/or oxygen; or in which the carbon-carbon bonding backbone is interrupted by bonding to groups of atoms containing nitrogen and/or oxygen, such as cyanurate ($C_3N_3O_3$). Thus, heterocarbons include, but are not limited to branched, straight-chain, cyclic and/or polycyclic aliphatic hydrocarbons, optionally containing ether functionality via oxygen atoms each of which is bound to two separate carbon atoms, tertiary amine functionality via nitrogen atoms each of which is bound to three separate carbon atoms, melamino groups and/or cyanurate groups; aromatic hydrocarbons; and arenes derived by substitution of the aforementioned aromatics with branched or straight chain alkyl, alkenyl, alkynyl, aryl and/or aralkyl groups.

Representative examples of G include —$(CH_2)_m$— wherein m is 1 to 12; diethylene cyclohexane; 1,2,4-triethylene cyclohexane; diethylene benzene; phenylene; —$(CH_2)_p$— wherein p is 1 to 20, which represent the terminal straight-chain alkyls further substituted terminally at the other end, such as —$CH_2$—, —$CH_2CH_2$—, —$CH_2CH_2CH_2$—, and —$CH_2CH_2CH_2CH_2CH_2CH_2CH_2CH_2$—, and their beta-substituted analogs, such as —$CH_2(CH_2)_qCH(CH_3)$—, where q is zero to 17; —$CH_2CH_2C(CH_3)_2CH_2$—; the structure derivable from methallyl chloride, —$CH_2CH(CH_3)CH_2$—; any of the structures derivable from divinylbenzene, such as —$CH_2CH_2(C_6H_4)CH_2CH_2$— and —$CH_2CH_2(C_6H_4)CH(CH_3)$—, where the notation $C_6H_4$ denotes a disubstituted benzene ring; any of the structures derivable from dipropenylbenzene, such as —$CH_2CH(CH_3)(C_6H_4)CH(CH_3)CH_2$—, where the notation $C_6H_4$ denotes a disubstituted benzene ring; any of the structures derivable from butadiene, such as —$CH_2CH_2CH_2CH_2$—, —$CH_2CH_2CH(CH_3)$—, and —$CH_2CH(CH_2CH_3)$—; any of the structures derivable from piperylene, such as —$CH_2CH_2CH_2CH(CH_3)$—, —$CH_2CH_2CH(CH_2CH_3)$—, and —$CH_2CH(CH_2CH_2CH_3)$—; any of the structures derivable from isoprene, such as —$CH_2CH(CH_3)CH_2CH_2$—, —$CH_2CH(CH_3)CH(CH_3)$—, —$CH_2C(CH_3)(CH_2CH_3)$—, —$CH_2CH_2CH(CH_3)CH_2$—, —$CH_2CH_2C(CH_3)_2$— and —$CH_2CH[CH(CH_3)_2]$—; any of the isomers of —$CH_2CH_2$-norbornyl-, —$CH_2CH_2$-cyclohexyl-; any of the diradicals obtainable from norbornane, cyclohexane, cyclopentane, tetrahydrodicyclopentadiene, or cyclododecene by loss of two hydrogen atoms; the structures derivable from limonene, —$CH_2CH(4$-methyl-$1$-$C_6H_9$—)$CH_3$, where the notation $C_6H_9$ denotes isomers of the trisubstituted cyclohexane ring lacking substitution in the 2 position; any of the monovinyl-containing structures derivable from trivinylcyclohexane, such as —$CH_2CH_2(vinylC_6H_9)CH_2CH_2$— and —$CH_2CH_2(vinylC_6H_9)CH(CH_3)$—, where the notation $C_6H_9$ denotes any isomer of the trisubstituted cyclohexane ring; any of the monounsaturated structures derivable from myrcene containing a trisubstituted C=C, such as —$CH_2CH[CH_2CH_2CH=C(CH_3)_2]CH_2CH_2$—, —$CH_2CH[CH_2CH_2CH=C(CH_3)_2]CH(CH_3)$—, —$CH_2C[CH_2CH_2CH=C(CH_3)_2](CH_2CH_3)$—, —$CH_2CH_2C[CH_2CH_2CH=C(CH_3)_2]CH_2$—, —$CH_2CH_2(C—)(CH_3)[CH_2CH_2CH=C(CH_3)_2]$, and —$CH_2CH[CH(CH_3)[CH_2CH_2CH=C(CH_3)_2]]$—; and any of the monounsaturated structures derivable from myrcene lacking a trisubstituted C=C, such as —$CH_2CH(CH=CH_2)CH_2CH_2CH_2C(CH_3)_2$—, —$CH_2CH(CH=CH_2)CH_2CH_2CH[CH(CH_3)_2]$—, —$CH_2C(=CH—CH_3)CH_2CH_2CH_2C(CH_3)_2$—, —$CH_2C(=CH—CH_3)CH_2CH_2CH[CH(CH_3)_2]$—, —$CH_2CH_2C(=CH_2)CH_2CH_2CH_2C(CH_3)_2$—, —$CH_2CH_2C(=CH_2)CH_2CH_2CH[CH(CH_3)_2]$—, —$CH_2CH=C(CH_3)_2CH_2CH_2CH_2C(CH_3)_2$—, and —$CH_2CH=C(CH_3)_2CH_2CH_2CH[CH(CH_3)_2]$.

Representative examples of R groups are H, branched and straight-chain alkyls of 1 to 20 carbon atoms such as methyl, ethyl, propyl, isopropyl, butyl, octenyl, cyclohexyl, phenyl, benzyl, tolyl, allyl, methoxyethyl, ethoxyethyl dimethylaminoethyl, cyanoethyl, and the like. In another embodiment, representative $R^{10}$ and $R^{11}$ groups are hydrogen, methyl, and ethyl, of which hydrogen and methyl are most preferred. In yet another embodiment, representative $R^1$ and $R^2$ groups can be hydrogen, methyl, ethyl, propyl. In still another embodiment, representative examples of $R^3$, $R^4$, $R^5$, $R^6$, $R^7$, and $R^8$ groups can be $H_2$, $C_1$ to $C_4$ straight chain or branched alkyls such as methyl, ethyl, propyl, isopropyl, butyl, isobutyl, pentyl, hexyl, heptyl, octyl, and aryl such as phenyl, benzyl, etc.

Specific examples of X are methoxy, ethoxy, propoxy, isopropoxy, isobutoxy, acetoxy, methoxyethoxy, and oximato, as well as the monovalent alkoxy groups derived from diols, known as "dangling diols", specifically, groups containing an alcohol and an alkoxy, such as —O—$CH_2CH$—OH), such as ethylene glycol, propylene glycol, neopentyl glycol, 1,3-propanediol, 2-methyl-1,3-propanediol, 1,3-butanediol, 2-methyl-2,4-pentanediol, 1,4-butanediol, cyclohexane dimethanol, and pinacol. In another embodiment, specific examples of X are methoxy, acetoxy and ethoxy, as well as the monovalent alkoxy groups derived from the diols, ethylene glycol, propylene glycol, neopentyl glycol, 1,3-propanediol, 2-methyl-1,3-propanediol, 1,3-butanediol, and 2-methyl-2,4-pentanediol.

Specific examples of $Z^b$ and $Z^c$ can be the divalent alkoxy groups derived from diols, such as ethylene glycol, propylene glycol, neopentyl glycol, 1,3-propanediol, 2-methyl-1,3-propanediol, 1,3-butanediol, 2-methyl-2,4-pentanediol, 1,4-butanediol, cyclohexane dimethanol, and pinacol. In another embodiment, specific examples of $Z^b$ and $Z^c$ are the divalent alkoxy groups derived from the diols such as ethylene glycol, propylene glycol, neopentyl glycol, 1,3-propanediol, 2-methyl-1,3-propanediol, 1,3-butanediol, and 2-methyl-2,4-pentanediol are preferred. The divalent alkoxy groups derived from the diols, 1,3-propanediol, 2-methyl-1,3-propanediol, 1,3-butanediol, and 2-methyl-2,4-pentanediol. The bridging ($Z^b$) content of the cyclic and bridging organofunctional silane compositions herein must be kept sufficiently low to prevent excessive average molecular weights and crosslinking, which would lead to gelation.

Additional embodiments are wherein v and w in Formulas 1 can be such that the ratio of w/v is between 1 and 9; X is RO—, RC(=O)O—; $Z^b$ and $Z^c$ can be derived from the diols, 1,3-propanediol, 2-methyl-1,3-propanediol, 1,3-butanediol, 2-methyl-2,4-pentanediol; R is alkyls of $C_1$ to $C_4$ and H; and G is a divalent straight chain alkyl of 2 to 18 carbon atoms. Other embodiments include those wherein w/v is between 2 and 8; X is ethoxy or one or more of the dangling diols derived from the diols, 1,3-propanediol, 2-methyl-1,3-propanediol, 1,3-butanediol, and 2-methyl-2,4-pentanediol; and G is a $C_2$-$C_{12}$ straight-chain alkyl derivative. Another embodiment are wherein v in Formula 1 is 0; X is RO—, RC(=O)O—; R is alkyls of $C_1$ to $C_4$ and H; and G is a divalent straight chain alkyl of 2 to 18 carbon atoms.

Representative examples of the cyclic and bridging dialkoxy organofunctional silanes described in the present invention include 2-(2-methyl-2,4 pentanedialkoxyethoxysilyl)-1-propyl amine; 2-(2-methyl-2,4-pentanedialkoxyisopropoxysilyl)-1-propyl mercaptan; 2-(2-methyl-2,4-pentanedialkoxymethylsilyl)-1-propyl chloride; 2-(2-methyl-2,4-pentanedialkoxyphenylsilyl)-1-propyl bromide; 3-(1,3-butanedialkoxyethoxysilyl)-1-propyl iodide; 3-(1,3-butanedialkoxyisopropoxysilyl)-1-propyl chloride; N-[3-(1,3-propanedialkoxyethoxysilyl)-1-propyl]phenylamine; N-[3-(1,3-propanedialkoxyisopropoxysilyl)-1-propyl]methylamine; 3-(1,2-propanedialkoxyethoxysilyl)-1-propyl glycidyl ether and 3-(1,2-propanedialkoxyisopropoxysilyl)-1-propyl methacrylate, both derivable from propylene glycol; 3-(1,2-ethanedialkoxyethoxysilyl)-1-propyl acrylate and 3-(1,2-ethanedialkoxyisopropoxysilyl)-1-propyl acetate, both derivable from ethylene glycol; 3-(neopentyl glycoxyethoxysilyl)-1-propyl amine and 3-(neopentyl glycoxyisopropoxysilyl)-1-propyl glycidyl ether, both derivable from neopentyl glycol; 3-(2,3-dimethyl-2,3-butanedialkoxyethoxysilyl)-1-propyl acrylate and 3-(2,3-dimethyl-2,3-butanedialkoxyisopropoxysilyl)-1-propyl methacrylate, both derivable from pinacol; 3-(2,2-diethyl-1,3-propanedialkoxyethoxysilyl)-1-propyl mercaptan; S-[3-(2,2-diethyl-1, propanedialkoxyisopropoxysilyl)-1-propyl]ethylthioether; bis[3-(2-methyl-1,3-propanedialkoxyethoxysilyl)-1-propyl]disulfide; bis[3-(2-methyl-1,3-propanedialkoxyisopropoxysilyl)-1-propyl] trisulfide; bis[3-(1,3-butanedialkoxymethylsilyl)-1-propyl] tetrasulfide; bis[3-(1,3-propanedialkoxymethylsilyl)-1-propyl]thioether; 3-(1,3-propanedialkoxyphenylsilyl)-1-propyl glycidyl thioether; tris-N,N',N"-[3-(1,2-propanedialkoxymethylsilyl)-1-propyl]melamine and tris-N,N',N"-[3-(1,2-propanedialkoxyphenylsilyl)-1-propyl]melamine, both derivable from propylene glycol; 3-(1,2-ethanedialkoxymethylsilyl)-1-propyl chloride and 3-(1,2-ethanedialkoxyphenylsilyl)-1-propyl bromide, both derivable from ethylene glycol; 3-(neopentyl glycoxymethylsilyl)-1-propyl acetate and 3-(neopentyl glycoxyphenylsilyl)-1-propyl octanoate, both derivable from neopentyl glycol; 3-(2,3-dimethyl-2,3-butanedialkoxymethylsilyl)-1-propyl amine and 3-(2,3-dimethyl-2,3-butanedialkoxyphenylsilyl)-1-propyl amine, both derivable from pinacol; 3-(2,2-diethyl-1,3-propanedialkoxymethylsilyl)-1-propyl acrylate; 3-(2,2-diethyl-1,3-propanedialkoxyphenylsilyl)-1-propyl methacrylate; 3-(2-methyl-1,3-propanedialkoxyethylsilyl)-1-propyl glycidyl ether; 3-(2-methyl-1,3-propanedialkoxyphenylsilyl)-1-propyl acetate; 2-(2-methyl-2,4-pentanedialkoxyethoxysilyl)-1-ethyl acrylate; 2-(2-methyl-2,4-pentanedialkoxymethoxysilyl)-1-ethyl bromide; 2-(2-methyl-2,4-pentanedialkoxy methylsilyl)-1-ethyl benzenesulfonate; 2-methyl-2,4-pentanedialkoxyethoxysilylmethyl methacrylate; 2-methyl-2,4-pentanedialkoxyisopropoxysilylmethyl bromide; neopentylglycoxypropoxysilylmethyl amine; propyleneglycoxymethylsilylmethyl mercaptan; neopentylglycoxyethylsilylmethyl glycidyl ether; 2-(neopentylglycoxyisopropoxysilyl)-1-ethyl butyrate; 2-(neopentylglycoxy methylsilyl)-1-ethyl propionate; 2-(1,3-butanedialkoxymethylsilyl)-1-ethyl acrylate; 3-(1,3-butanedialkoxyisopropoxysilyl)-4-butyl methacrylate; 3-(1,3-butanedialkoxyethylsilyl)-1-propyl mercaptan; 3-(1,3-butanedialkoxymethylsilyl)-1-propyl methanesulfonate; 6-(2-methyl-2,4-pentanedialkoxyethoxysilyl)-1-hexyl amine; 1-(2-methyl-2,4-pentanedialkoxyethoxysilyl)-5-hexyl acrylat; 8-(2-methyl-2,4-pentanedialkoxyethoxysilyl)-1-octyl methacrylate; 10-(2-methyl-2,4-pentanedialkoxyethoxysilyl)-1-decyl glycidyl ether; 3-(2-methyl-2,4-pentanedialkoxyethoxysilyl)-1-propyl trifluoromethanesulfonate; 3-(2-methyl-2,4-pentanedialkoxypropoxysilyl)-1-propyl amine; N-[3-(2-methyl-2,4-pentanedialkoxyisopropoxysilyl)-1-propyl]ethylene diamine; tris-N,N',N"-[3-(2-methyl-2,4-pentanedialkoxybutoxysilyl)-1-propyl]diethylene triamine; tetrakis-N,N',N",N'"-[3-(2-methyl-2,4-pentanedialkoxyisopropoxysilyl)-1-propyl]triethylene tetramine; bis-(3-(2-methyl-2,4-pentanedialkoxyethoxysilyl)-1-propyl) sulfide; 6-(1,3-butanedialkoxyethoxysilyl)-1-hexyl amine; 1-(1,3-butanedialkoxyethoxysilyl)-5-hexyl glycidyl ether; 8-(1,3-butanedialkoxyethoxysilyl)-1-octyl acrylate; 10-(1,3-butanedialkoxyethoxysilyl)-1-decyl methacrylate; and bis-(3-(2-methyl-2,4-pentanedialkoxyethoxysilyl)-1-propyl) thioether.

In another embodiment, the cyclic dialkoxy organofunctional silanes are cyclic and bridging dialkoxy analogs to the 3-chloro-1-propyltriethoxysilane (3-triethoxysilyl-1-propyl chloride), used as a starting point for the manufacture of silane coupling agents as, for example, polysulfide silanes, such as triethoxysilylpropyl tetrasulfide referred to herein as TESPT, triethoxysilylpropyl .disulfide referred to herein as TESPD. The cyclic and bridging dialkoxy haloalkyl silanes are novel and excellent alternatives to 3-triethoxysilyl-1-propyl chloride for use where reduced VOC emissions are desired.

The cyclic and bridging dialkoxy organofunctional silane compositions included herein may comprise single components or various mixtures of individual cyclic and bridging dialkoxy organofunctional silane components, organofunctional silane components, which contain only monofunctional alkoxy groups, and optionally including other species as well. Synthetic methods result in a distribution of various silanes, wherein mixtures of the starting components are employed for the purpose of generating mixtures of cyclic and bridging dialkoxy organofunctional silane products. Moreover, it is understood that the partial hydrolyzates and/or condensates of these cyclic and bridging dialkoxy organofunctional silanes, also referred to as cyclic and bridging dialkoxy organofunctional siloxanes and/or silanols, may be encompassed by the silanes herein as a side product of most methods of manufacture of the cyclic and bridging dialkoxy organofunctional silanes. Also, the partial hydrolyzates and/or condensates can occur upon storage of the cyclic and bridging dialkoxy organofunctional silanes, especially in humid conditions, or under conditions in which residual water remaining from their preparation is not completely removed subsequent to their preparation. Furthermore, partial to substantial hydrolysis of the cyclic and bridging dialkoxy organofunctional silanes may be deliberately prepared by incorporating the appropriate stoichiometry or excess of water into the methods of preparation described herein for the silanes. Also, the siloxane content of the cyclic and bridging dialkoxy organofunctional silanes may be deliberately prepared by incorporating the appropriate stoichiometry or excess of water into the methods of preparation for the silanes described herein. Silane structures herein encompassing hydrolyzates and siloxanes are described in the structures given in Formula 1 wherein the subscripts, v, of $Z^b$=(—O—)$_{0.5}$ and/or u, of X=OH can be substantive, meaning substantially larger than zero.

The cyclic and bridging dialkoxy organofunctional silane compositions, if liquid, may be loaded on a carrier or a mixture of more than one carrier, such as a porous polymer, carbon black, or an inorganic filler, such as silica, alumina, various clays, etc. By loading the composition on a carrier it is in solid form for delivery to the rubber formulation. In another embodiment, the carrier would be part of the filler, either intimately absorbed onto or within, or chemically bound to the filler.

The silane compounds with heterocyclic silicon groups included herein may be prepared by transesterification of organofunctional alkoxy-substituted silanes and diols with or without a catalyst, by the esterification of organofunctional silyl halides with diols, or by the hydrosilylation of substituted alkenes with a hydrosilane containing a heterocylic silicon group to generate cyclic and bridging silane compositions.

The transesterification of organofunctional alkoxy-substituted silanes and diols may be conducted with or without a catalyst. The catalyst may be an acid, a base or a transition metal catalyst. Suitable acid catalysts are hydrochloric acid, p-toluenesulfonic acid and the like. Typical base catalysts are sodium methoxide, sodium ethoxide. Suitable transition metal catalysts are tetraisopropyl titanate, dibutyltin dilaurate.

During esterification of organofunctional silyl halides with diols, diols are added to the silyl halide with removal of the hydrogen halide formed. The hydrogen halide may be removed by sparging with nitrogen or by using reduced pressure. Any remaining halo groups can be removed by the addition of an alcohol such as methanol, ethanol, isopropanol, and the like.

In another embodiment of the present invention, the diol-derived organofunctional silane can be prepared by reacting a catalyzed mixture of organofunctional silane reactant and diol with simultaneous distillation. The reaction leads to the alcohol exchange of one or more of the alkoxy groups selectively at the silicon atom of the organofunctical silane reactant with the diol. The reaction is driven by the removal of the more volatile by-product alcohol by distillation. Suitable catalysts include acids such as p-toluenesulfonic acid, sulfuric acid, hydrochloric acid, chlorosilanes, chloroacetic acids, phosphoric acid, their mixtures, and so forth; bases such as sodium ethoxide; and, transition metal-containing catalyts such as titanium alkoxides, titanium-containing chelates, zirconium alkoxides, zirconium-containing chelates and mixtures thereof.

In yet another embodiment of the present invention, the diol-derived organofunctional silane can be prepared by catalyzing a mixture of organofunctional silane and diol, in a first embodiment, at a molar ratio of at least about 0.5 moles of diol per alkoxy-silyl group to be transesterified, in a second embodiment, at a molar ratio of from about 0.5 to about 1.5 for a trialkoxy silane; and, in a third embodiment, from about 1.0 to about 1.5 for a trialkoxy silane. In each of the foregoing embodiments, the reaction temperature can range from about 10° C. to about 150° C. and in another embodiment from about 30° C. to 90° C. while maintaining a pressure in the range of from about 0.1 to about 2000 mm Hg absolute, and in another embodiment, from about 1 to about 80 mm Hg absolute. Excess diol can be utilized to increase reaction rate.

In another embodiment the diol-derived organofunctional silane can be prepared by slowly adding diol to organofunctional silane in the presence of catalyst at the desired reaction temperature and under vacuum. If desired, a neutralization step may be utilized to neutralize any acid or base catalyst that may have been utilized thereby improving product storage.

Optionally, an inert solvent may be used in the process. The solvent may serve as a diluent, carrier, stabilizer, refluxing aid or heating agent. Generally, any inert solvent, i.e., one which does not enter into the reaction or adversely affect the reaction, may be used. In one embodiment, solvents are those which are liquid under normal conditions and have a boiling point below about 150° C. Examples include aromatics, hydrocarbons, ethers, aprotic solvents and chlorinated hydrocarbon solvents such as, toluene, xylene, hexane, butane, diethyl ether, dimethylformamide, dimethyl sulfoxide, carbon tetrachloride, methylene chloride, and so forth.

In another embodiment of the present invention, the diol-derived organofunctional silane can be prepared by continuously premixing the flow-streams of organofunctional silane reactant, diol, and catalyst (when employed) at appropriate ratios and then introducing the premixed reactants into a reactive distillation system, in one embodiment, a thin film distillation device operating at the desired reaction temperature and vacuum conditions. Conducting the reaction in a thin film under vacuum accelerates the removal of the alcohol by-product and improves the transesterification reaction rate. The vaporization and removal of the by-product alcohol from the film shifts the chemical equilibrium of the reaction to favor formation of the desired product and minimizes undesired side reactions.

The foregoing embodiment of the process herein comprises the steps of:

a) reacting, in a thin film reactor, a thin film reaction medium comprising organofunctional silane, e.g., a thiocarboxylate silane, diol and catalyst to provide diol-derived organofunctional silane and by-product alcohol;

b) vaporizing the by-product alcohol from the thin film to drive the reaction;

c) recovering the diol-derived organofunctional silane reaction product;

d) optionally, recovering the by-product alcohol by condensation; and, e) optionally, neutralizing the diol-derived organofunctional silane product to improve its storage stability.

The molar ratio of diol to organofunctional silane reactant used in the foregoing continuous thin film process will depend upon the number of alkoxy groups that are desired to be replaced with diol. In one embodiment of the thin film process, a stoichiometric equivalent molar ratio of 1 is used wherein one diol replaces two alkoxy groups. Generally, for the practice of this embodiment, the molar ratio of diol to organofunctional silane can be varied within a range of from about 95 to about 125 percent of stoichiometric equivalence for each alkoxy-silyl group to be transesterified. In a particular embodiment, the molar ratio of diol to organofunctional silane can be within the range of from about 100 to about 110 percent of stoichiometric equivalence. In another embodiment, the molar ratio can be within a range of from about 100 to about 105 percent of stoichiometric equivalence for the molar ratio of diol to organofunctional silane. Those skilled in the art will recognize that excess diol could be utilized to increase reaction rates but such is ordinarily of no significant advantage when conducting the reaction in a thin film and only adds to the expense.

The apparatus and method of forming the film are not critical and can be any of those known in the art. Typical known devices include falling film or wiped film evaporators. Minimum film thickness and flow rates will depend on the minimum wetting rate for the film forming surface. Maximum film thickness and flow rates will depend on the flooding point for the film and apparatus. Vaporization of the alcohol from the film is effected by heating the film, by reducing pressure over the film or by a combination of both. It is preferred that mild heating and reduced pressure are utilized to form the diol-derived organofunctional silane of this invention. Optimal temperatures and pressures (vacuum) for running the thin film process will depend upon the specific starting organofunctional silane's alkoxy groups and diol used in the process. Additionally, if an optional inert solvent is used in the process, that choice will affect the optimal temperatures and pressures (vacuum) utilized.

The by-product alcohol vaporized from the film is removed from the reactive distillation apparatus by a standard partial vacuum-forming device and can be condensed, collected and recycled as feed to other processes. The diol-derived organofunctional silane product is recovered by standard means from the reactive distillation apparatus as a liquid phase. If an inert solvent has been used or if additional purification is necessary or desirable, the diol-derived organofunctional silane product may be fed to another similar distillation apparatus or distillation column to effect that separation. Optionally, the product may be neutralized to improve product storage.

The diol-derived organofunctional silane compounds of the present invention are useful as crosslinkers, coupling agents, adhesion promoters, as intermediates for the preparation of other silane compounds and as filler treating agents. Illustrative compositions into which the silane compounds may be incorporated include rubber, industrial and architectural coatings, wood coatings, hard coats, adhesion promoting primers for paints or adhesives, UV or EB cured acrylic coatings, adhesives and sealants, polyester resin systems used to form reinforced composites with fiberglass, carbon or polyphenylene terephalamide (Kevlar™, E.I. DuPont, Wilm., Del.) reinforcements, RTV silicones, and generally in any application where an organofunctional silane would be used. As is clear to one of ordinary skill in the art, there is a vast array of applications of the present invention in rubber, coating, sealant, adhesives, masonry sealers, fiberglass binders and sizes, inks and other systems that typically use organofunctional silanes.

The diol-derived organofunctional silane compositions herein provide significant advantages over traditional coupling agents, adhesion promoters and crosslinking agents, which have found extensive use in the known art. These cyclic and bridging organofunctional silane compositions reduce the about of volatile components that are generated during use. The volatile components are safety hazards and pollute the environment. The traditional coupling agents include, for example, polysulfide silanes such as TESPT and TESPD. These contain in their molecular structures three ethoxy groups on each silicon atom, which results in the release of up to three moles of ethanol for each silane silicon equivalent during the rubber manufacturing process in which the silane silicon couples to the filler. The release of ethanol is a great disadvantage because it is flammable and therefore poses a threat of fire, and because it contributes so greatly to VOC emissions and is therefore potentially harmful to the environment. The diol-derived organofunctional silane compositions described herein eliminate or greatly mitigate this problem by capping the ethanol emissions to only one, less than one, or even essentially zero moles of ethanol per silane equivalent. They accomplish this because the silane ethoxy groups are replaced with diol-derived alkoxy groups and thus diols are released during the rubber manufacture process in place of much of or nearly all of the ethanol released. The diols, having boiling points well in excess of rubber processing temperatures, are not vaporized out of the rubber during the rubber manufacture process as is the ethanol, but are retained by the rubber where they migrate to the silica surface due to their high polarity and become hydrogen bonded to the also polar silica surface. The presence of the diols on the silica surface then leads to further advantages not obtainable with ethanol (due to its volatility and ejection during the rubber compounding process) in the subsequent cure process, in which the presence of the diol bound to the silica surface prevents the silica surface from binding the curatives and thereby interfering with the cure. Traditional silanes not based on diols require more curatives to counter losses due to silica binding.

The addition of hydrocarbon based diols to the rubber compounding formulation prior to and/or concurrent with the addition of curatives is of advantage for the efficient utilization of the curatives, in particular, and polar substances, such as, but not limited to, amines, amides, sulfenamides, thiurams, and guanidines. Whether diols are exclusively added in the form of diol-derived silanes or as free diols in combination with the silane coupling agents, the polarity of the diols is of advantage to the rubber compounding process. These polar substances tend to migrate to the filler surface due to dipole interactions with the filler. This tends to make them unavailable for their intended function within the organic polymer matrix, where their functions include such things as vulcanization and/or coupling initiation, acceleration, retardation, or sulfur atom transfer and/or activation. The hydrocarbon backbone based diols enhance the function of the curatives by interfering with their tendency to bind to the silica surface, thereby forcing them into the rubber matrix to perform their function. The hydrocarbon based diols accomplish this by themselves being very polar, and thereby by themselves binding to the filler surface, leaving less room for the curatives to bind to filler. The hydrocarbon based diols thus act as curative displacing agents from the filler. The short chain of the preferred hydrocarbon based diols further enhances their function by a chelate effect. Chains of two or three carbon atoms between the two OH groups of the diol promote the formation of 5- or 6-membered rings when both oxygen atoms bind to a common atom, such as a proton residing on the filler. This dual binding to a common center, known as, and referred to herein as the chelate effect, further enhances the affinity of the diol to the filler and thereby enhances its ability to prevent the binding of the curatives to the filler.

Those hydrocarbon based diols used herein whose $R^{10}$ and $R^{11}$ groups are hydrocarbon-derived, are superior to ether- and/or polyether-based monofunctional alcohols or difunctional alcohols (diols) because the lack of the ether functionality of these hydrocarbon based diols avoids the problems typically encountered with ethers. These problems include high toxicity, their tendency for spontaneous peroxide formation, and high chain lengths between OH groups. Spontaneous peroxide formation is a problem because it is difficult to prevent, and because the peroxides lead to flammability hazards. Furthermore, the peroxides decompose when heated to free radicals, which can initiate unwanted side reactions in the rubber polymers. These side reactions include peroxide-induced cure chemistries, in which polymer chains are crosslinked. This can lead to premature, excess, and variable crosslinking during or prior to cure. The excess crosslinking can lead to inferior properties in the rubber, premature crosslinking can lead to scorch, and the variability makes it hard to fabricate a reproducible rubber composition and any articles of manufacture derived thereof. The excess chain lengths of the ether-containing diols forces chelation by the two OH groups to involve ring sizes of at least about 8 atoms, which is well beyond the optimum 5 or 6, accessible to hydrocarbon based diols. Chelation involving an OH group and an ether, which would give the optimum 5 or 6 membered rings, is not as strong as chelation with the two OH groups accessible to the hydrocarbon based diols because the OH groups are less sterically hindered and because the OH groups are more active at forming hydrogen bond interactions, which are key to binding the diols to the filler surface.

In one embodiment, one or more of the cyclic and bridging dialkoxy organofunctional silane compositions are mixed with the organic polymer before, during or after the compounding of the filler into the organic polymer. In a second embodiment, the addition of silanes can occur before or during the compounding of the filler into the organic polymer, because these silanes facilitate and improve the dispersion of the filler. The total amount of silane present in the resulting combination should be about 0.05 to about 25 parts by weight per hundred parts by weight of organic polymer (phr); more preferably 1 to 10 phr. In one embodiment, fillers can be used in quantities ranging from about 5 to about 100 phr. In a second embodiment fillers can be used in quantities from 25 to 80 phr.

In practice, sulfur vulcanized rubber products typically are prepared by thermomechanically mixing rubber and various ingredients in a sequentially step-wise manner followed by shaping and curing the compounded rubber to form a vulcanized product. First, the rubber(s) and various rubber compounding ingredients are blended in at least one, and often in the case of silica filled low rolling resistance tires, two, preparatory thermomechanical mixing stage(s) in suitable mixers. Such preparatory mixing is referred to as nonproductive mixing or non-productive mixing steps or stages. In one embodiment, such preparatory mixing usually is conducted at temperatures up to about 140° C. to about 200° C. and often up to about 150° C. to about 180° C. Subsequent to such preparatory mix stages, in a final mixing stage, sometimes referred to as a productive mixing stage, curing agents, and possibly one or more additional ingredients, are mixed with the rubber compound or composition, typically at a temperature in a range of about 50° C. to about 130° C., this is a lower temperature than the temperatures utilized in the preparatory mix stages. The lower temperature used in the final mixing stage prevents or retards premature curing of the sulfur curable rubber, which is sometimes referred to as scorching of the rubber composition. The rubber mixture, referred to as a rubber compound or composition, typically is allowed to cool, either after or during the intermediate process referred to as mill mixing, this cooling process occurs between the aforesaid various mixing steps, for example, to a temperature of about 50° C. or lower. When it is desired to mold and to cure the rubber, the rubber is placed into the appropriate mold at least about 130° C. and up to about 200° C., which will cause the vulcanization of the rubber by the organofunctional groups on the silane(s) and any other free sulfur sources in the rubber mixture.

By thermomechanical mixing, it is meant that the rubber compound, or composition of rubber and rubber compounding ingredients, is mixed in a rubber mixture under high shear conditions where it autogeneously heats up as a result of the mixing primarily due to shear and associated friction within the rubber mixture in the rubber mixer. Several chemical reactions involving the silane may occur at various steps in the mixing and curing processes. The first reaction is a relatively fast reaction and is considered herein to take place between the filler and the hydrolyzable groups of the cyclic and bridging dialkoxy organofunctional silane composition(s). Such reaction may occur at a relatively low temperature, for example, at about 120° C. The subsequent reactions are considered herein to be the reactions, which takes place between the organofunctional group(s) of the silane composition(s) and the sulfur vulcanizable rubber at a higher temperature, for example, above about 140° C. Another key chemical reaction, which takes place, is the crosslinking of the polymer chains by forming chemical bonds with the elemental sulfur added to the curatives. This crosslinking process actually takes place by a number of individual chemical reactions involving also other materials added to the rubber composition, particularly in the curatives.

Another sulfur source may be used, for example, in the form of elemental sulfur as $S_8$. A sulfur donor is considered herein as a sulfur-containing compound, which liberates free, or elemental sulfur, at a temperature in a range of about 140° C. to about 190° C. Such sulfur donors may be, for example, although are not limited to, polysulfide vulcanization accelerators and organosilane polysulfides with at least two connecting sulfur atoms in its polysulfide bridge. The amount of free sulfur source addition to the mixture can be controlled or manipulated as a matter of choice relatively independently from the addition of the aforesaid cyclic and bridging dialkoxy organofunctional silane compositions. Thus, for example, the independent addition of a sulfur source may be manipulated by the amount of addition thereof and by sequence of addition relative to addition of other ingredients to the rubber mixture.

Addition of an alkyl silane to the coupling agent system, the cyclic and bridging dialkoxy organofunctional silane compositions plus additional free sulfur source and/or vulcanization accelerator, typically in a mole ratio of alkyl silane to cyclic and bridging dialkoxy organofunctional silane in a range of 1/50 to 1/2 promotes an even better control of rubber composition processing and aging.

In one embodiment the preparation of a rubber composition comprises the sequential steps of:

a) thermomechanically mixing, in at least one preparatory mixing step, under effective mixing conditions, e.g., at a temperature from about 120° C. to about 200° C. in a first embodiment and from about 140° C. to about 190° C. in a second embodiment, for a total mixing time of from about 2 to about 20 minutes in a first embodiment and from about 4 to about 15 minutes in a second embodiment for such mixing step(s):

b) about 100 parts by weight of at least one sulfur vulcanizable rubber selected from conjugated diene homopolymers and copolymers, and copolymers of at least one conjugated diene and aromatic vinyl compound, i) from about 5 to about 100 phr (parts per hundred rubber of a particulate filler in a first embodiment and from about 25 to about 80 phr of a particulate filler in a second embodiment, wherein the particulate filler contains from 0 to about 85 weight percent carbon black, ii) from about 0.05 to about 20 parts by weight of filler (ii) of at least one cyclic and bridging dialkoxy organofunctional silane composition; and, optionally, c) subsequently blending therewith, in a final thermomechanical mixing step under effective blending conditions, e.g., at a temperature of from about 50° C. to about 130° C. for a time sufficient to blend the rubber, e.g., from about 1 to about 30 minutes in a first embodiment and from about 1 to about 3 minutes in a second embodiment, at least one curing agent or blend of curing agents in an amount of up to about 5 phr and curing said mixture under effective curing conditions, e.g., at a temperature of from about 130° C. to about 200° C. for a period of from about 5 to about 60 minutes.

In another embodiment, the preparation of a rubber composition may comprise the additional steps of preparing an assembly of a tire or sulfur vulcanizable rubber with a tread comprised of the rubber composition prepared according to this invention and vulcanizing the assembly at a temperature in a range of about 130° C. to about 200° C.

Suitable organic polymers and fillers are well known in the art and are described in numerous texts, of which two examples include *The Vanderbilt Rubber Handbook*; R. F. Ohm, ed.; R.T. Vanderbilt Company, Inc., Norwalk, Conn.; 1990 and *Manual For The Rubber Industry*; T. Kempermann, S. Koch, J. Sumner, eds.; Bayer A G, Leverkusen, Germany; 1993. Representative examples of suitable polymers include solution styrene-butadiene rubber (SSBR), styrene-butadiene rubber (SBR), natural rubber (NR), polybutadiene (BR), ethylene-propylene co- and ter-polymers (EP, EPDM), and acrylonitrile-butadiene rubber (NBR). The rubber composition is comprised of at least one diene-based elastomer, or rubber. Suitable conjugated dienes are isoprene and 1,3-butadiene and suitable vinyl aromatic compounds are styrene and alpha methyl styrene. Thus, the rubber is a sulfur curable rubber. Such diene based elastomer, or rubber, may be selected, for example, from at least one of cis-1,4-polyisoprene rubber (natural and/or synthetic), and preferably natural rubber), emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (about 35-50 percent vinyl), high vinyl polybutadiene rubber (about 50-75 percent vinyl), styrene/isoprene copolymers, emulsion polymerization prepared styrene/butadiene/acrylonitrile terpolymer rubber and butadiene/acrylonitrile copolymer rubber. An emulsion polymerization derived styrene/butadiene (E-SBR) might be used having a relatively conventional styrene content of about 20 to about 28 percent bound styrene or, for some applications, an E-SBR having a medium to relatively high bound styrene content, namely, a bound styrene content of about 30 to about 45 percent. Emulsion polymerization prepared styrene/butadiene/acrylonitrile terpolymer rubbers containing about 2 to about 40 weight percent bound acrylonitrile in the terpolymer are also contemplated as diene based rubbers for use in this invention.

The solution polymerization prepared styrene-butadiene rubber SBR (S-SBR) typically has a bound styrene content in a range of about 5 to about 50, preferably about 9 to about 36, percent. Polybutadiene elastomer may he conveniently characterized, for example, by having about at least a 90 weight percent cis-1,4-content.

Representative examples of suitable filler materials include metal oxides, such as silica (pyrogenic and precipitated), titanium dioxide, aluminosilicate and alumina, siliceous materials including clays and talc, and carbon black. Particulate, precipitated silica is also sometimes used for such purpose, particularly when the silica is used in connection with a silane. In some cases, a combination of silica and carbon black is utilized for reinforcing fillers for various rubber products, including treads for tires. Alumina can be used either alone or in combination with silica. The term "alumina" can be described herein as aluminum oxide, or $Al_2O_3$. The fillers may be hydrated or in anhydrous form. Use of alumina in rubber compositions can be shown, for example, in U.S. Pat. No. 5,116,886 and EP 631 982.

The cyclic and bridging dialkoxy organofunctional silane compositions may be premixed, or pre-reacted, with the filler particles or added to the rubber mix during the rubber and filler processing, or mixing stage. If the silane and filler are added separately to the rubber mix during the rubber and filler mixing, or processing stage, it is considered that the cyclic and bridging dialkoxy organofunctional silane compositions then couple in situ to the filler.

The vulcanized rubber composition should contain a sufficient amount of filler to contribute a reasonably high modulus and high resistance to tear. The combined weight of the filler may be as low as about 5 to about 100 phr, but is more preferably from about 25 to about 85 phr.

In one embodiment precipitated silicas are utilized as a filler. The silica may be characterized by having a BET surface area, as measured using nitrogen gas, preferably in the range of about 40 to about 600, and more usually in a range of about 50 to about 300 $m^2$/g. The BET method of measuring surface area is described in the *Journal of the American Chemical Society*, Volume 60, page 304 (1930). The silica typically may also be characterized by having a dibutylphthalate (DBP) absorption value in a range of about 100 to about 350, and more usually about 150 to about 300. Further, the silica, as well as the aforesaid alumina and aluminosilicate, may be expected to have a CTAB surface area in a range of about 100 to about 220. The CTAB surface area is the external surface area as evaluated by cetyl trimethylammonium bromide with a pH of about 9. The method is described in ASTM D 3849.

Mercury porosity surface area is the specific surface area determined by mercury porosimetry. For such technique, mercury is penetrated into the pores of the sample after a thermal treatment to remove volatiles. Set up conditions may be suitably described as using about a 100 mg sample, removing volatiles during about 2 hours at about 105° C. and ambient atmospheric pressure to about 2000 bars pressure measuring range. Such evaluation may be performed according to the method described in Winslow, Shapiro in ASTM bulletin, p. 39 (1959) or according to DIN 66133. For such an evaluation, a CARLO-ERBA Porosimeter 2000 might be used. The average mercury porosity specific surface area for the silica should be in a range of about 100 to about 300 $m^2$/g.

In one embodiment a suitable pore size distribution for the silica, alumina and aluminosilicate according to such mercury porosity evaluation is considered herein to be five percent or less of its pores have a diameter of less than about 10 nm; about 60 to about 90 percent of its pores have a diameter of about 10 to about 100 nm; about 10 to about 30 percent of its pores have a diameter at about 100 to about 1,000 nm; and about 5 to about 20 percent of its pores have a diameter of greater than about 1,000 nm.

In a second embodiment the silica may be expected to have an average ultimate particle size, for example, in the range of about 0.01 to about 0.05 μm as determined by the electron microscope, although the silica particles may be even smaller, or possibly larger, in size. Various commercially available silicas may be considered for use in this invention such as, from PPG Industries under the HI-SIL trademark with designations HI-SIL 210, 243, etc.; silicas available from Rhone-Poulenc, with, for example, designation of ZEOSIL 1165MP; silicas available from Degussa with, for example, designations VN2 and VN3, etc. and silicas commercially available from Huber having, for example, a designation of HUBERSIL 8745.

Where it is desired for the rubber composition, which contains both a siliceous filler such as silica, alumina and/or aluminosilicates and also carbon black reinforcing pigments, to be primarily reinforced with silica as the reinforcing pigment, the weight ratio of such siliceous fillers to carbon black can be about at least 3/1 and preferably about at least 10/1 and, thus, in a range of about 3/1 to about 30/1. The filler may be comprised of about 15 to about 95 weight percent precipitated silica, alumina and/or aluminosilicate and, correspondingly about 5 to about 85 weight percent carbon black, wherein the said carbon black has a CTAB value in a range of about 80 to about 150. Alternatively, the filler can be comprised of about 60 to about 95 weight percent of said silica, alumina and/or aluminosilicate and, correspondingly, about 40 to about 5 weight percent carbon black. The siliceous filler and carbon black may be pre-blended or blended together in the manufacture of the vulcanized rubber.

The rubber composition may be compounded by methods known in the rubber compounding art, such as mixing the various sulfur-vulcanizable constituent rubbers with various commonly used additive materials such as, for example, curing aids, such as sulfur, activators, retarders and accelerators, processing additives, such as oils, resins including tackifying resins, silicas, plasticizers, fillers, pigments, fatty acid, zinc oxide, waxes, antioxidants and antiozonants, peptizing agents, and reinforcing materials such as, for example, carbon black. Depending on the intended use of the sulfur vulcanizable and sulfur vulcanized material or rubber, the additives mentioned above are selected and commonly used in conventional amounts.

The vulcanization may be conducted in the presence of an additional sulfur vulcanizing agent. Examples of suitable sulfur vulcanizing agents include, for example elemental sulfur (free sulfur) or sulfur donating vulcanizing agents, for example, an amino disulfide, polymeric polysulfide or sulfur olefin adducts which are conventionally added in the final, productive, rubber composition mixing step. The sulfur vulcanizing agents, which are common in the art are used, or added in the productive mixing stage, in an amount ranging from about 0.4 to about 3 phr, or even, in some circumstances, up to about 8 phr, with a range of from about 1.5 to about 2.5 phr and sometimes from about 2 to about 2.5 phr.

Vulcanization accelerators, i.e., additional sulfur donors, may be used herein. It is appreciated that may include the following examples, benzothiazole, alkyl thiuram disulfide, guanidine derivatives and thiocarbamates. Representative of such accelerators can be, but not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine) and dithiobis(dibenzyl amine). Other additional sulfur donors may be, for example, thiuram and morpholine derivatives. Representative of such donors are, for example, but not limited to, dimorpholine disulfide, dimorpholine tetrasulfide, tetramethyl thiuram tetrasulfide, benzothiazyl-2, N-dithiomorpholide, thioplasts, dipentamethylenethiuram hexasulfide, and disulfidecaprolactam.

Accelerators are used to control the time and/or temperature required for vulcanization and to improve the properties of the vulcanizate. In one embodiment, a single accelerator system may be used, i.e., a primary accelerator. Conventionally and preferably, a primary accelerator(s) is used in total amounts ranging from about 0.5 to about 4, preferably about 0.8 to about 1.5 phr. Combinations of a primary and a secondary accelerator might be used with the secondary accelerator being used in smaller amounts (of 0.05 to 3 phr) in order to activate and to improve the properties of the vulcanizate. Delayed action accelerators may be used. Vulcanization retarders might also be used. Suitable types of accelerators are amines, disulfides, guanidines, thioureas, thiazoles, thiurams, sulfenamides, dithiocarbamates and xanthates. Preferably, the primary accelerator is a sulfenamide. If a second accelerator is used, the secondary accelerator can be a guanidine, dithiocarbamate or thiuram compound.

Typical amounts of tackifier resins, if used, comprise about 0.5 to about 10 phr, usually about 1 to about 5 phr. Typical amounts of processing aids comprise about 1 to about 50 phr. Such processing aids can include, for example, aromatic, napthenic, and/or paraffinic processing oils. Typical amounts of antioxidants comprise about 1 to about 5 phr. Representative antioxidants may be, for example, diphenyl-p-phenylenediamine and others, such as, for example, those disclosed in the *Vanderbilt Rubber Handbook* (1978), pages 344-346. Typical amounts of antiozonants, comprise about 1 to about 5 phr. Typical amounts of fatty acids, if used, which can include stearic acid, comprise about 0.5 to about 3 phr. Typical amounts of zinc oxide comprise about 2 to about 5 phr. Typical amounts of waxes comprise about 1 to about 5 phr. Often microcrystalline waxes are used. Typical amounts of peptizers comprise about 0.1 to about 1 phr. Typical peptizers may be, for example, pentachlorothiophenol and dibenzamidodiphenyl disulfide.

The rubber compositions of this invention can be used for various purposes. For example, it can be used for various tire compounds. Such tires can be built, shaped, molded and cured by various methods, which are known and will be readily apparent to those having skill in such art. One particularly useful application of the rubber compositions herein is for the manufacture of tire treads. An advantage of tires, tire treads, of other articles of manufacture derived from the rubber compositions herein is they suffer from less VOC emissions during their lifetime and use as a result of having been manufactured from a rubber compound which contains less residual silane ethoxy groups than do rubber compounds of the known and presently practiced art. This is a direct result of having used dialkoxy-functional silane coupling agents in their manufacture, which contain fewer or essentially no ethoxy groups on silicon, relative to the silane coupling agents of the currently known and practiced art. The lack or reduction of ethoxysilane groups in the coupling agents used results in fewer residual ethoxy groups on silicon after the article of manufacture is produced, from which fewer or no ethanol can be released by hydrolysis of the residual ethoxysilane groups by exposure of the article of manufacture to water during use.

The rubber compositions herein and the articles of manufacture derivable thereof as described herein are novel from those of the known and commonly practiced art in that both contain hydrocarbon backbone based diols, as defined herein. Typical examples of such species contained in the rubber compositions and articles of manufacture described herein include diols such as an isomer of propanediol, pentane diol, and such as ethylene glycol, and propylene glycol. Additional species would include stearate monoesters and/or diesters of these diols. These species possess polarities intermediate between those of the rubber polymers and the filler, thereby helping to stabilize the compositions and articles of manufacture from filler reagglomeration and the resulting degradation of the properties and performance parameters thereof.

Of the examples, which follow, Examples 1-4 are illustrative of the present invention. The invention may be better understood by reference to the following examples in which the parts and percentages are by weight unless otherwise indicated.

EXAMPLE 1

Preparation of Cyclic and Bridging Dialkoxy Organofunctional Silanes, 3-aminopropylethoxy-(1,3-butanedialkoxy)silane and 1,3-bis-(3-aminopropyl-1,3-butanedialkoxysilyloxy)butane To 221.3 grams (1 mole) of aminopropyltriethoxysilane in a 1 L three-necked flask were added 90.12 grams (1 mole) of 1,3-butanediol and 1 gram of a 21% weight solution of sodium ethoxide in ethanol. The mixture was placed under vacuum and heated to 30° C. Ethanol distilled from the reaction mixture and was collected in the receiver flask resulting in 203.7 grams of a mixture by GC of 4.4% 3-aminopropyltriethoxysilane, 72.6% 3-aminopropylethoxy(1,3-butanedialkoxy)silane, 2.1% bis-[3-aminopropyl(1,3-butanedialkoxy)disiloxane and 19.4% 1,3-bis-[3-aminopropyl(1,3-butanedialkoxy)silyloxy)butane.

EXAMPLE 2

Preparation of Cyclic and Bridging Dialkoxy Organofunctional Silanes, 3-aminopropylethoxy(2-methyl-1,3-propanedialkoxy)silane and 1,3-bis-[3-aminopropyl(2-methyl-1,3-propanedialkoxy)siloxy]-2-methylpropane To 221.3 grams (1 mole) of aminopropyltriethoxysilane in a 1 L three-necked flask were added 90.1 grams (1 mole) of 2-methyl-1,3-propanediol and 1 grams of a 21% weight solution of sodium ethoxide in ethanol. The mixture was placed under vacuum and heated to 90° C. Ethanol was collected in the receiver flask resulting in 204.7 grams of a mixture by GC of 5.3% 3-aminopropyltriethoxysilane, 88.6% 3-aminopropylethoxy(2-methyl-1,3-propanedialkoxy)silane and 2.5% 1,3-bis-[3-aminopropyl(2-methyl-1,3-propanedialkoxy)siloxy]-2-methylpropane.

EXAMPLE 3

Preparation of Cyclic and Bridging Dialkoxy Organofunctional Silane, 3,4-epoxycyclohexylmethoxy(2-methyl-1,3-propanedialkoxy)silane, bis-[3,4-epoxycyclohexylmethoxy(2-methyl-1,3-propanedialkoxy)]disiloxane and 1,3-bis-(3,4-epoxycyclohexyl(2-methyl-1,3-propanedialkoxysiloxy)2-methylpropane To 52.2 grams (0.2 mole) of trimethoxysilylethylcyclohexene oxide in a 100 ml three-necked flask were added 19.2 grams (0.2 moles) of 2-methyl-1,3-propanediol and 0.25 grams of a 21% weight solution of sodium ethoxide in ethanol. The mixture was placed under vacuum and heated to 40° C. Methanol was collected in the receiver flask resulting in 59.4 grams of a mixture by GC of 10.7% 3,4-epoxycyclohexylethyltrimethoxysilane, 73.4% 3,4-epoxycyclohexylmethoxy(2-methyl-1,3-propanedialkoxy)silane, 6.4% bis-[3,4-epoxycyclohexylmethoxy(2-methyl-1,3-propanedialkoxy)]disiloxane and 3.4% 1,3-bis-(3,4-epoxycyclohexyl(2-methyl-1,3-propanedialkoxysiloxy)2-methylpropane.

EXAMPLE 4

Preparation of bis(3-(2-methyl-2,4-pentanedioxyethoxysilyl)-1-propyl disulfane from 2-methyl-2,4-pentanediol and bis(3-triethoxysilylpropyl)disulfane A 5-Liter round bottom flask equipped with a mechanical agitator, condenser (connected to a vacuum pump), dropping funnel, internal thermometer, and heating mantle, was charged with 2844 g (6.0 mol) of bis(3-triethoxysilylpropyl) disulfane and heated to 43° C. 0.852 g Sulfuric acid was added and the mixture was stirred well. The pressure in the reaction flask was reduced to 50 mm Hg and 1416 g (12.0 mol) 2-methyl-2,4-pentanediol were added from the dropping funnel over 4 hrs. The mixture was maintained at 43-48° C. and 50-70 mm Hg until reaction completion. Ethanol formed during the diol addition was continuously removed from the reaction flask, condensed, and collected. Sodium ethylate (2.71 g, 21% solution in ethanol) was added to the flask to neutralize the acid catalyst, and the product was cooled to room temperature. The precipitated salts were removed by filtration to yield 2982.0 g of product (94.5% yield).

Gel permeation chromatography analysis showed Mn=490 and Mw=540, consistent with desired product formation.

EXAMPLE 5

Preparation of bis(3-(2-methyl-2,4-pentanedioxyethoxysilyl)-1-propyl tetrasulfane from 2-methyl-2,4-pentanediol and bis(3-triethoxysilylpropyl)tetrasulfane A 5-Liter round bottom flask equipped with a mechanical agitator, condenser (connected to a vacuum pump), dropping funnel, internal thermometer, and heating mantle, was charged with 2959 g (5.5 mol) of bis-(3-triethoxysilylpropyl) tetrasulfane and heated to 41° C. 2.13 g Sulfuric acid was added and the mixture was stirred well. The pressure in the reaction flask was reduced to 75 mm Hg and 1298.0 g (11.0 mol) 2-methyl-2,4-pentanediol were added from the dropping funnel over 4 hrs. The mixture was maintained at 46-49° C. and 50-80 mm Hg until reaction completion. Ethanol formed during the diol addition was continuously removed from the reaction flask, condensed, and collected. Sodium ethylate (5.32 g, 21% solution in ethanol) was added to the flask to neutralize the acid catalyst, and the product was cooled to room temperature. The precipitated salts were removed by filtration to yield 2805 g of product (86.5% yield).

High pressure liquid chromatography analysis showed some unreacted sulfane starting material. Gel permeation chromatography analysis showed Mn=530 and Mw=610, consistent with desired product formation.

EXAMPLE 6

Preparation of 3-(2-methyl-2,4-pentanedioxyethoxysilyl)-1-propanethiol from 2-methyl-2,4-pentanediol and 3-(triethoxysilyl)-1-propanethiol A 250-ml round bottom flask equipped with a magnetic stir bar, water condenser (connected to a vacuum pump), dropping funnel, internal thermometer, and heating mantle, was charged with 122.2 grams 3-(triethoxysilyl)-1-propanethiol (98.5%, 0.505 mol), 111 mg of paratoluenesulfonic acid, and 61.02 grams 2-methyl-2,4-pentanediol (99%, 0.511 mol). The reaction flask content was heated to 33 C and vacuum (11 mm Hg) was applied, in order to remove ethanol formed. The temperature was raised to 60 C after 2 hours, to complete the reaction and remove any remaining ethanol. The temperature was raised to 60 C after 2 hours, to complete the reaction and remove any remaining ethanol. 135.6 grams of 3-(2-methyl-2,4-pentanedioxyethoxysilyl)-1-propanethiol product (84% purity, 0.431 mol, 99.2% yield) were obtained.

EXAMPLE 7

Preparation of Rubber Using Cyclic and Bridging Organofunctional Silanes from Examples 4 and 5

A typical silica-rubber SBR formulation was used (Table 1). Mixing was carried out in a 1.6 liter "B" type Banbury with tangential rotors. Silquest®A-1589 (TESPD) and Silquest® A-1289 (TESPT) were chosen as control. The silane loadings were adjusted to a constant alkoxysilane silicon loading.

TABLE 1

Silica-Silane/Rubber Formulation

| Ingredient | PHR |
|---|---|
| sSBR (Buna VSL 5525-1) - (Bayer AG) | 103.2 |
| BR (Budene 1207) - (Goodyear) | 25 |
| silica - Zeosil 1165MP, (Rhodia) | variable |
| A-1589 and A-1289 | variable |
| Silanes from Examples 4 and 5 | variable |
| oil - Sundex 8125 (Sun Oil) | 5.0 |
| zinc oxide - Kadox 720C (ZincCorp.) | 2.5 |
| stearic acid - Industrene R (Witco, Crompton) | 1.0 |
| 6 PPD - Flexzone 7P (Uniroyal, Crompton) | 2.0 |
| Wax - Sunproof Improved (Uniroyal, Crompton) | 1.5 |
| Hardness modifiers (carbon-black, fumed silica and accelerators) | variable |
| Final Mix Ingredients | |
| Rubbermakers Sulfur 104, Harwick | 1.4 |
| CBS - Delac S (Uniroyal, Crompton) | 1.7 |
| DPG - (Uniroyal, Crompton) | 2.0 |

TABLE 2

Procedure for Two-Non productive mix steps
TWO PASS PROCEDURE

| Step | Procedure |
|---|---|
| | First Banbury pass: cooling with water @ 25° C., 72% fill factor |
| 1. | Add polymers, RDM (ram down mix) 30 seconds @ 117 RPM |
| 2. | Add 50% silica, all silane, RDM 30 seconds |
| 3. | Add remaining 50% silica, oil, RDM 30 seconds |
| 4. | Dust down, RDM 20 seconds |
| 5. | Dust down, RDM 20 seconds |
| 6. | Dust down, RDM* @ higher speeds to 160-170° C. (approx. 1 minute) Total time for first pass is approx. 5-6 minutes. |
| 7. | Dump, sheet off roll mill @ 50-60° C., cool below 60° C. Second Banbury pass: |
| 1. | Add compound from 1st pass, RDM 30 seconds @ 117 RPM |
| 2. | Add remainder of ingredients, RDM 30 seconds |
| 3. | Dust down, RDM to 160-170° C. (in approx. 2 minutes) by increasing rotor speed. |
| 4. | Hold at 170° C. (or higher temperature) for 8 minutes by changing speeds on mixer. Total time for second Banbury pass is approx. 11-12 minutes. |
| 5. | Dump, sheet off roll mill @ 50-60° C. to cool |

*RDM: Ram down mix time

Productive Mix

Sulfur and accelerators (primary and secondary) were added to the above masterbatch on a two-roll mill at 50-60° C.

The controls, Silquest® A-1289, A-1589 (TESPD) and the silanes from Examples 4 and 5 were mixed in two non-productive mix steps which included an intermediate cooling step. After all silica, silane and oil ingredients were incorporated into the mix, the rpm of the rotors was raised so as to achieve the desired silanization temperature. The mix was then held at that temperature for 8 minutes. For polysulfide silanes, a cooling step is generally needed before this silanization step (sometimes even multiple cooling steps). The mix procedures are set forth in Table 2, above. Curing and testing were done according to ASTM standards. In addition, small strain dynamic tests were carried out on a Rheometrics Dynamic Analyzer (ARES-Rheometrics Inc.).

| Measurement/Procedure | Compound Testing Standards |
|---|---|
| Mooney viscosity and scorch | ASTM D1646 |
| Oscillating disc rheometry | ASTM D2084 |
| Curing of test plaques | ASTM D3182 |
| Stress-strain properties | ASTM D412 |
| Heat build-up | ASTM D623 |

Dynamic Mechanical Properties

Payne effect strain sweeps were carried out from dynamic strain amplitudes of 0.01% to about 25% shear strain amplitude at 10 Hz and 60° C. The dynamic parameters, $G'_{initial}$, $\Delta G'$, $G''_{max}$, $\tan \delta_{max}$ were extracted from the non-linear responses of the rubber compounds at small strains. In some cases, steady state values of $\tan \delta$ were measured after 15 minutes of dynamic oscillations at strain amplitudes of 35% (at 60° C.). Temperature dependence of dynamic properties were also measured from about −80° C. to +80° C. at small strain amplitudes (1 or 2%) at a frequency of 10 Hz.

TABLE 3

Rubber Compounding Data

| Rubber Composition | A | B | C | D | E | F |
|---|---|---|---|---|---|---|
| Silane | A-1289 | A-1589 | Example 4 | Example 4 | Example 5 | Example 5 |
| Silane Loading (p.h.r) | 6.4 | 5.8 | 5.8 | 6.5 | 6.4 | 7.1 |
| Mooney Properties | | | | | | |
| Viscosity at 100° C. (ML1 + 4) | 79.1 | 73.63 | 67.6 | 66.76 | 70.69 | 67.46 |
| MV at 135° C. (MS1+) | 34.36 | 31.83 | 30.15 | 29.59 | 32.68 | 32.26 |

TABLE 3-continued

Rubber Compounding Data

| Rubber Composition | A | B | C | D | E | F |
|---|---|---|---|---|---|---|
| Silane | A-1289 | A-1589 | Example 4 | Example 4 | Example 5 | Example 5 |
| Silane Loading (p.h.r) | 6.4 | 5.8 | 5.8 | 6.5 | 6.4 | 7.1 |
| Scorch at 135° C. (MS1 + $t_3$) (min) | 6.56 | 9.25 | 10.32 | 10.03 | 7.06 | 6.43 |
| Cure at 135° C. (MS1 + $t_{18}$) (min) | 9.52 | 12.4 | 15.08 | 12.32 | 10.2 | 10.06 |
| Rheometer (ODR) Properties, (1° arc at 149° C.) | | | | | | |
| $M_L$ (dN-m) | 8.92 | 8.64 | 8.46 | 8 | 8.55 | 8.46 |
| $M_H$ (dN-m) (30 min. timer) | 28.1 | 27.04 | 26.26 | 26.26 | 29.48 | 29.3 |
| t90 (min) (30 min. timer) | 20.52 | 19.3 | 13.14 | 12.57 | 17.56 | 13.25 |
| $t_{s1}$ (min) | 4.2 | 5.23 | 5.34 | 5.36 | 4.15 | 4.2 |
| Physical Properties, (cured t90 at 149° C.) | | | | | | |
| Hardness (Shore A) | 56 | 60 | 55 | 62 | 63 | 62 |
| Rubber Composition | A | B | C | D | E | F |
| Tensile (MPa) | 21 | 23 | 23 | 24 | 24 | 24 |
| Elongation (%) | 462 | 605 | 644 | 671 | 537 | 578 |
| 25% Modulus (MPa) | 0.81 | 0.84 | 0.86 | 0.91 | 0.92 | 0.91 |
| 100% Modulus (MPa) | 1.92 | 1.64 | 1.7 | 1.8 | 2.1 | 2.1 |
| 300% Modulus (MPa) | 10.9 | 7.9 | 7.5 | 8.3 | 10.8 | 10.3 |
| Reinforcement Index, (300%/100%) | 5.7 | 4.8 | 4.4 | 4.6 | 5.1 | 4.9 |
| Non-linearity (0-10%) 60° C. | | | | | | |
| $G'_{initial}$ (MPa) | 3.36 | 4.96 | 5.73 | 5.78 | 4.85 | 3.94 |
| $\Delta G'$ (MPa) | 1.66 | 2.87 | 3.61 | 3.57 | 2.70 | 2.08 |
| $G''_{max}$ (MPa) | 0.397 | 0.602 | 0.72 | 0.709 | 0.578 | 0.439 |
| $\tan\delta_{max}$ | 0.171 | 0.203 | 0.189 | 0.183 | 0.189 | 0.177 |
| Temperature Dependence | | | | | | |
| $\tan\delta$ 0° C. | 0.424 | 0.389 | 0.393 | 0.429 | 0.412 | 0.433 |
| G' 0° C. (MPa) | 6.31 | 9.29 | 9.87 | 9.973 | 8.96 | 7.65 |
| G' 60° C. (MPa) | 2.28 | 3.26 | 3.19 | 3.23 | 3.09 | 2.62 |
| $\tan\delta$ 60° C. | 0.152 | 0.167 | 0.171 | 0.168 | 0.167 | 0.155 |

While the invention has been described with reference to a number of embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A silane of the general formula:

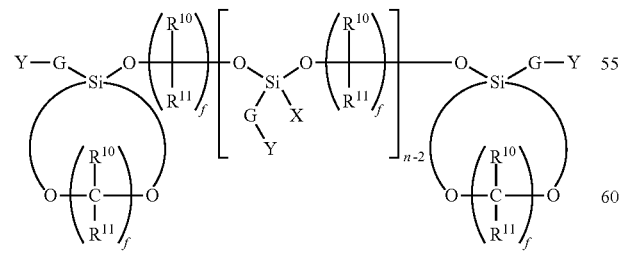

wherein each occurrence of G is independently a polyvalent group derived from an alkyl, alkenyl, aryl or aralkyl group with G containing from 1 to 30 carbon atoms;

each occurrence of $R^{10}$ and $R^{11}$ is independently a hydrogen, an alkyl group, an alkenyl group, an aryl group, an aralkyl group, or a monovalent heterocarbon group containing 1 to about 20 carbon atoms;

each occurrence of Y is independently a monovalent organofunctional group chosen from the group consisting of mercapto, acryloxy, methacryloxy, —O—$CH_2$—$C_2H_3O$, —$C_6H_9O$, —$CR^6$(—O—)$CR^4R^5$, —$NH_2$, —$NHR^4$, —$NR^4R^5$, —$NR^4$-$L^1$-$NR^5R^6$, —$NR^4$-$L^1$(-$NR^5R^6$)$_2$, —$NR^4$-$L^1$-$NR^5$-$L^2$-$NR^6R^7$, —$NR^4$-$L^1$(-$NR^5R^6$)$_3$, —$NR^4$-$L^1$-$NR^5$-$L^2$-$NR^6$-$L^3$-$NR^7R^8$, and —$NR^4$-$L^1$-N(-$L^2NR^5R^6$)$_2$, wherein each occurrence of $L^1$, $L^2$ and $L^3$ is selected independently from the meanings given for G and each occurrence of $R^4$, $R^5$, $R^6$, $R^7$ and $R^8$ is independently a hydrogen, an alkyl group, an alkenyl group, an aryl group, an aralkyl group, or a monovalent heterocarbon group containing 1 to about 20 carbon atoms;, each occurrence of X is independently selected from the group consisting of —Cl, —Br, $R^1O$—, $R^2C$(=O)O—, $R^1R^2C$=NO—, $R^1R^2NO$—, $R^1R^2N$—, —$R^1$, -(OSi$R^1R^2$)$_t$(OSi$R^1R^2R^3$), and —O($R^{10}CR^{11}$)$_t$OH, wherein each occurrence of $R^1$, $R^2$, and $R^3$ is independently selected from the group consisting of straight alkyl, cyclic alkyl, branched alkyl, alkenyl, aryl, aralkyl group containing from 1 to 20 carbon atoms, and hydrogen;

each occurrence of the subscript f is independently an integer from 1 to 15;

each occurrence of the subscript t is independently an integer from 0 to 50; and the subscript n is an integer from 3 to 100.

2. The silane of claim 1 wherein G is selected from the group consisting of diethylene cyclohexane, diethylene benzene, phenylene, $-(CH_2)_m-$ wherein m is an integer from 1 to 12, and $-CH_2(CH_2)_qCH(CH_3)-$ wherein q is an integer from zero to 17.

3. The silane of claim 1 wherein each occurrence of $-O(R^{10}CR^{11})_fO-$ is independently selected from divalent alkoxy groups derived from 1,3-propanediol, 2-methyl-1,3-propanediol, 1,3-butanediol and 2-methyl-2,4-pentanediol.

4. The silane of claim 1 wherein $R^{10}$ and $R^{11}$ is each independently selected from a group consisting of hydrogen, methyl, ethyl and propyl.

5. The silane of claim 1 wherein X is $R^1O-$ or $-O(R^{10}CR^{11})_fOH$, wherein $R^1$ is independently selected from the group consisting of straight alkyl, cyclic alkyl, branched alkyl, alkenyl, aryl, aralkyl group containing from 1 to 20 carbon atoms and hydrogen; each occurrence of $R^{10}$ and $R^{11}$ is independently a hydrogen, an alkyl group, an alkenyl group, an aryl group, an aralkyl group, or a monovalent heterocarbon group containing 1 to about 20 carbon atoms; and each occurrence of the subscript f is independently an integer from 1 to 15.

6. A silane of the general formula:

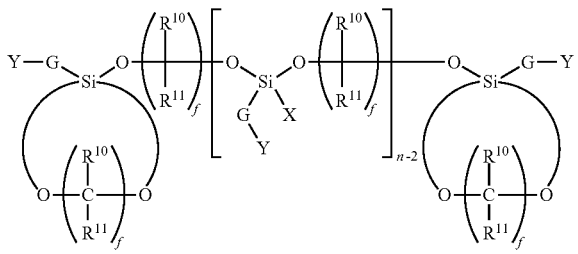

wherein each occurrence of G is independently a polyvalent group derived from an alkyl, alkenyl, aryl or aralkyl group with G containing from 1 to 30 carbon atoms;

each occurrence of $R^{10}$ and $R^{11}$ is independently a hydrogen, an alkyl group, an alkenyl group, an aryl group, an aralkyl group, or a monovalent heterocarbon group containing 1 to about 20 carbon atoms;

each occurrence of Y is independently a monovalent organofunctional group chosen from the group consisting of $-OH$, $-NR^4C(=O)OR^5$, $-OC(=O)NR^4R^5$, $-NR^4C(=O)SR^5$, $-SC(=O)NR^4R^5$, $-NR^4C(=S)OR^5$, $-OC(=S)NR^4R^5$, $-NR^4C(=S)SR^5$, $-SC(=S)NR^4R^5$, maleimide, maleate, substituted maleate, fumurate, substituted fumurate, $-CN$, citraconimide, $-OCN$, $-N=C=O$, $-SCN$, $-N=C=S$, $-OR^4$, $SR^4$, $-S-SR^4$, $-S-S-SR^4$, $-S-S-S-SR^4$, $-S-S-S-S-SR^4$, $-S-S-S-S-S-SR^4$, $-S_xR^4$, $-SC(=S)OR^4$, $-SC(=S)SR^4$, $-SC(=O)SR^4$, $-NR^4C(=O)NR^5R^6$, $-NR^4C(=S)NR^5R^6$, $R^4C(=O)NR^5-$, $-C(=O)NR^4R^5$, $R^4C(=S)NR^4-$, melamine and cyanurato wherein each occurrence of $R^4$, $R^5$, and $R^6$ is independently a hydrogen, an alkyl group, an alkenyl group, an aryl group, an aralkyl group, or a monovalent heterocarbon group containing 1 to about 20 carbon atoms; and each occurrence of X is independently selected from the group consisting of $-Cl$, $-Br$, $R^1O-$, $R^2C(=O)O-$, $R^1R^2C=NO-$, $R^1R^2NO-$, $R^1R^2N-$, $-R^1$, $-(OSiR^1R^2)_t(OSiR^1R^2R^3)$, and $-O(R^{10}CR^{11})_fOH$, wherein each occurrence of $R^1$, $R^2$, and $R^3$ is independently selected from the group consisting of straight alkyl, cyclic alkyl, branched alkyl, alkenyl, aryl, aralkyl group containing from 1 to 20 carbon atoms, and hydrogen;

each occurrence of the subscript f is independently an integer from 1 to 15;

each occurrence of the subscript t is independently an integer from 0 to 50; and the subscript n is an integer from 3 to 100.

7. The silane of claim 6 wherein G is selected from the group consisting of diethylene cyclohexane, diethylene benzene, phenylene, $-(CH_2)_m-$ wherein m is an integer from 1 to 12 and $-CH_2(CH_2)_qCH(CH_3)-$ wherein q is an integer from zero to 17.

8. The silane of claim 6 wherein each occurrence of $-O(R^{10}CR^{11})_fO-$ is independently selected from divalent alkoxy groups derived from 1,3-propanediol, 2-methyl-1,3-propanediol, 1,3-butanediol, and 2-methyl-2,4-pentanediol.

9. The silane of claim 6 wherein X is $R^1O-$ or $-O(R^{10}CR^{11})_fOH$, wherein $R^1$ is independently selected from the group consisting of straight alkyl, cyclic alkyl, branched alkyl, alkenyl, aryl, aralkyl group containing from 1 to 20 carbon atoms and hydrogen; each occurrence of $R^{10}$ and $R^{11}$ is independently a hydrogen, an alkyl group, an alkenyl group, an aryl group, an aralkyl group, or a monovalent heterocarbon group containing 1 to about 20 carbon atoms; and each occurrence of the subscript f is independently an integer from 1 to 15.

10. A silane of the general formula:

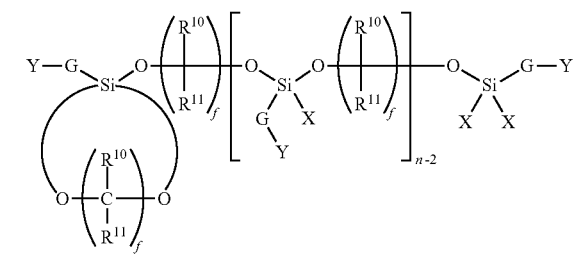

wherein each occurrence of G is independently a polyvalent group derived from an alkyl, alkenyl, aryl or aralkyl group with G containing from 1 to 30 carbon atoms;

each occurrence of $R^{10}$ and $R^{11}$ is independently a hydrogen, an alkyl group, an alkenyl group, an aryl group, an aralkyl group, or a monovalent heterocarbon group containing 1 to about 20 carbon atoms;

each occurrence of Y is independently a monovalent organofunctional group chosen from the group consisting of mercapto, acryloxy, methacryloxy, $-O-CH_2-C_2H_3O$, $-C_6H_9O$, $-CR^6(-O-)CR^4R^5$, $-NH_2$, $-NHR^4$, $-NR^4R^5$, $-NR^4-L^1-NR^5R^6$, $-NR^4-L^1(-NR^5R^6)_2$, $-NR^4-L^1-NR^5-L^2-NR^6R^7$, $-NR^4-L^1(-NR^5R^6)_3$, $-NR^4-L^1-NR^5-L^2-NR^6-L^3-NR^7R^8$, and $-NR^4-L^1-N(-L^2NR^5R^6)_2$, wherein each occurrence of $L^1$, $L^2$ and $L^3$ is selected independently from the meanings given for G and each occurrence of $R^4$, $R^5$, $R^6$, $R^7$ and $R^8$ is independently a hydrogen, an alkyl group, an alkenyl group, an aryl group, an aralkyl group, or a monovalent heterocarbon group containing 1 to about 20 carbon atoms;

each occurrence of X is independently selected from the group consisting of —Cl, —Br, $R^1O$—, $R^2C(=O)O$—, $R^1R^2C=NO$—, $R^1R^2NO$—, $R^1R^2N$—, —$R^1$, —$(OSiR^1R^2)_t(OSiR^1R^2R^3)$, and —$O(R^{10}CR^{11})_fOH$, wherein each occurrence of $R^1$, $R^2$, and $R^3$ is independently selected from the group consisting of straight alkyl, cyclic alkyl, branched alkyl, alkenyl, aryl, aralkyl group containing from 1 to 20 carbon atoms and hydrogen;

each occurrence of the subscript f is independently an integer from 1 to 15;

each occurrence of the subscript t is independently and integer from 0 to 50; and the subscript n is an integer from 3 to 100.

11. The silane of claim 10 wherein G is selected from the group consisting of diethylene cyclohexane, diethylene benzene, phenylene, —$(CH_2)_m$— wherein m is 1 to 12 and —$CH_2(CH_2)_qCH(CH_3)$— wherein q is zero to 17.

12. The silane of claim 10 wherein each occurrence of —$O(R^{10}CR^{11})_fO$— is independently selected from divalent alkoxy groups derived from 1,3-propanediol, 2-methyl-1,3-propanediol, 1,3-butanediol and 2-methyl-2,4-pentanediol.

13. The silane of claim 10 wherein $R^{10}$ and $R^{11}$ is each independently selected from a group consisting of hydrogen, methyl, ethyl and propyl.

14. The silane of claim 10 wherein X is $R^1O$— or —$O(R^{10}CR^{11})_fOH$, wherein $R^1$ is independently selected from the group consisting of straight alkyl, cyclic alkyl, branched alkyl, alkenyl, aryl, aralkyl group containing from 1 to 20 carbon atoms and hydrogen; each occurrence of $R^{10}$ and $R^{11}$ is independently a hydrogen, an alkyl group, an alkenyl group, an aryl group, an aralkyl group, or a monovalent heterocarbon group containing 1 to about 20 carbon atoms; and each occurrence of the subscript f is independently an integer from 1 to 15.

15. A silane of the general formula:

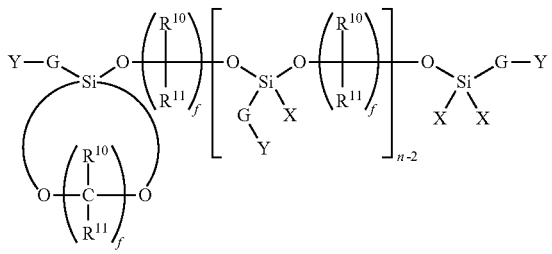

wherein
each occurrence of G is independently a polyvalent group derived from an alkyl, alkenyl, aryl or aralkyl group with G containing from 1 to 30 carbon atoms;

each occurrence of $R^{10}$ and $R^{11}$ is independently a hydrogen, an alkyl group, an alkenyl group, an aryl group, an aralkyl group, or a monovalent heterocarbon group containing 1 to about 20 carbon atoms;

each occurrence of Y is independently a monovalent organofunctional group chosen from the group consisting of —OH, —$NR^4C(=O)OR^5$, —$OC(=O)NR^4R^5$, —$NR^4C(=O)SR^5$, —$SC(=O)NR^4R^5$, —$NR^4C(=S)OR^5$, —$OC(=S)NR^4R^5$, —$NR^4C(=S)SR^5$, —$SC(=S)NR^4R^5$, maleimide, maleate, substituted maleate, fumurate, substituted fumurate, —CN, citraconimide, —OCN, —N=C=O, —SCN, —N=C=S, —$OR^4$—$SR^4$, —S—$SR^4$, —S—S—$SR^4$, —S—S—S—$SR^4$, —S—S—S—S—$SR^4$, —S—S—S—S—S—$SR^4$, —$S_xR^4$, —$SC(=S)OR^4$, —$SC(=S)SR^4$, —$SC(=O)SR^4$, —$NR^4C(=O)NR^5R^6$, —$NR^4C(=S)NR^5R^6$, $R^4C(=O)NR^5$—, —$C(=O)NR^4R^5$—, $R^4C(=S)NR^4$—, melamine and cyanurato wherein each occurrence of $R^4$, $R^5$, and $R^6$ is independently a hydrogen, an alkyl group, an alkenyl group, an aryl group, an aralkyl group, or a monovalent heterocarbon group containing 1 to about 20 carbon atoms; and each occurrence of X is independently selected from the group consisting of —Cl, —Br, $R^1O$—, $R^2C(=O)O$—, $R^1R^2C=NO$—, $R^1R^2NO$—, $R^1R^2N$—, —$R^1$, —$(OSiR^1R^2)_t(OSiR^1R^2R^3)$, and —$O(R^{10}CR^{11})_fOH$, wherein each occurrence of $R^1$, $R^2$, and $R^3$ is independently selected from the group consisting of straight alkyl, cyclic alkyl, branched alkyl, alkenyl, aryl, aralkyl group containing from 1 to 20 carbon atoms, and hydrogen;

each occurrence of the subscript f is independently an integer from 1 to 15;

each occurrence of the subscript t is independently an integer from 0 to 50; and the subscript n is an integer from 3 to 100.

16. The silane of claim 15 wherein G is selected from the group consisting of diethylene cyclohexane, diethylene benzene, phenylene, —$(CH_2)_m$— wherein m is an integer from 1 to 12 and —$CH_2(CH_2)_qCH(CH_3)$— wherein q is an integer from zero to 17.

17. The silane of claim 15 wherein each occurrence of —$O(R^{10}CR^{11})_fO$— is independently selected from divalent alkoxy groups derived from 1,3-propanediol, 2-methyl-1,3-propanediol, 1,3-butanediol, and 2-methyl-2,4-pentanediol.

18. The silane of claim 15 wherein X is $R^1O$— or —$O(R^{10}CR^{11})_fOH$, wherein $R^1$ is independently selected from the group consisting of straight alkyl, cyclic alkyl, branched alkyl, alkenyl, aryl, aralkyl group containing from 1 to 20 carbon atoms and hydrogen; each occurrence of $R^{10}$ and $R^{11}$ is independently a hydrogen, an alkyl group, an alkenyl group, an aryl group, an aralkyl group, or a monovalent heterocarbon group containing 1 to about 20 carbon atoms; and each occurrence of the subscript f is independently an integer from 1 to 15.

19. A sizing for fiberglass comprising the silane of claim 1.

20. A sizing for fiberglass comprising the silane of claim 16.

21. A sizing for fiberglass comprising the silane of claim 10.

22. A sizing for fiberglass comprising the silane of claim 15.

23. A rubber composition comprising
(a) at least one sulfur vulcanizable rubber selected from the group consisting of a conjugated diene homopolymer and a copolymer, a copolymer of at least one conjugated diene and aromatic vinyl compound, and mixtures thereof;
(b) at least one particulate filler;
(c) least one silane of claim 1; and, optionally, at least one curing agent.

24. A rubber composition comprising
(a) at least one sulfur vulcanizable rubber selected from the group consisting of a conjugated diene homopolymer and a copolymer, a copolymer of at least one conjugated diene and aromatic vinyl compound, and mixtures thereof;
(b) at least one particulate filler;
(c) least one silane of claim 6; and, optionally, at least one curing agent.

25. A rubber composition comprising
(a) at least one sulfur vulcanizable rubber selected from the group consisting of a conjugated diene homopolymer and a copolymer, a copolymer of at least one conjugated diene and aromatic vinyl compound, and mixtures thereof;
(b) at least one particulate filler;
(c) east one silane of claim 10; and, optionally, at least one curing agent.

26. A rubber composition comprising
(a) at least one sulfur vulcanizable rubber selected from the group consisting of a conjugated diene homopolymer and a copolymer, a copolymer of at least one conjugated diene and aromatic vinyl compound, and mixtures thereof;
(b) at least one particulate filler;
(c) east one silane of claim 15; and, optionally, at least one curing agent.

27. The cured rubber composition of claim 23.
28. The cured rubber composition of claim 24.
29. The cured rubber composition of claim 25.
30. The cured rubber composition of claim 26.

* * * * *